US012606827B2

(12) United States Patent
Adorno et al.

(10) Patent No.: US 12,606,827 B2
(45) Date of Patent: Apr. 21, 2026

(54) COMPOUNDS FOR TREATMENT OF OSTEOARTHRITIS

(71) Applicant: Altos Labs, Inc., Redwood City, CA (US)

(72) Inventors: Maddalena Adorno, Menlo Park, CA (US); Benedetta Nicolis Di Robilant, Redwood City, CA (US); Amit Umesh Joshi, Sunnyvale, CA (US)

(73) Assignee: Altos Labs, Inc., Redwood City, CA (US)

( * ) Notice: Subject to any disclaimer, the term of this patent is extended or adjusted under 35 U.S.C. 154(b) by 481 days.

(21) Appl. No.: 18/320,575

(22) Filed: May 19, 2023

(65) Prior Publication Data

US 2024/0124876 A1 Apr. 18, 2024

Related U.S. Application Data

(63) Continuation of application No. PCT/US2021/060201, filed on Nov. 19, 2021.

(60) Provisional application No. 63/116,619, filed on Nov. 20, 2020.

(51) Int. Cl.

| | |
|---|---|
| ***C12N 15/113*** | (2010.01) |
| ***A61K 9/00*** | (2006.01) |
| ***A61K 35/28*** | (2015.01) |
| ***A61P 19/02*** | (2006.01) |
| ***A61P 29/00*** | (2006.01) |
| ***C12N 5/0775*** | (2010.01) |
| ***C12N 15/86*** | (2006.01) |

(52) U.S. Cl.
CPC .......... *C12N 15/113* (2013.01); *A61K 9/0019* (2013.01); *A61K 35/28* (2013.01); *A61P 19/02* (2018.01); *A61P 29/00* (2018.01); *C12N 5/0662* (2013.01); *C12N 15/86* (2013.01); *C12N 2310/14* (2013.01); *C12N 2750/14143* (2013.01)

(58) Field of Classification Search
CPC .. C12P 17/06; C12P 7/62; C12P 17/04; C12N 9/16; C12N 9/93; C12Y 301/0202; C12Y 602/01003
See application file for complete search history.

(56) References Cited

FOREIGN PATENT DOCUMENTS

| | | | |
|---|---|---|---|
| EP | 2572721 | A1 | 3/2013 |
| WO | WO-2014144752 | A1 | 9/2014 |
| WO | WO-2015128651 | A1 | 9/2015 |
| WO | WO-2016176493 | A1 | 11/2016 |
| WO | WO-2022109341 | A1 | 5/2022 |

OTHER PUBLICATIONS

PCT/US2021/060201 International Search Report and Written Opinion dated Mar. 11, 2022.

*Primary Examiner* — Paul J Holland
(74) *Attorney, Agent, or Firm* — Sterne, Kessler, Goldstein & Fox P.L.L.C.

(57) ABSTRACT

The present disclosure relates to methods of treating osteoarthritis in a subject in need thereof, the method comprising administering to the subject a therapeutically effective amount of a USP16 inhibitor.

20 Claims, 20 Drawing Sheets

Specification includes a Sequence Listing.

OA - Osteoarthritis patient
HD - Healthy age-matched controls

OA - Osteoarthritis patient
HD - Healthy age-matched controls

OA - Osteoarthritis patient; HD - Healthy age-matched controls

COMPOUNDS FOR TREATMENT OF OSTEOARTHRITIS

CROSS-REFERENCE TO RELATED APPLICATIONS

This application is a continuation of International Application No. PCT/US2021/060201, filed Nov. 19, 2021, which claims the benefit of U.S. Provisional Application No. 63/116,619, filed on Nov. 20, 2020, both of which are incorporated herein by reference in their entirety.

SEQUENCE LISTING

The instant application contains a Sequence Listing which has been submitted electronically in XML format and is hereby incorporated by reference in its entirety. Said XML copy, created on May 18, 2023, is named 57267_702_301_SL.xml and is 20,818 bytes in size.

BACKGROUND OF THE INVENTION

Osteoarthritis (OA) is a highly prevalent musculoskeletal disorder affecting 303 million people globally in 2017. Since OA is associated with aging and obesity which are on the rise in global population, its prevalence is also dramatically increasing. Currently there is no treatment that can prevent, stop, or even restrain progression of OA; the current OA pain medications have a number of side effects that increase the disease burden. Hence, there is a need for therapies which can prevent, stop, or reverse the progression of OA.

SUMMARY OF THE INVENTION

In some embodiments the present disclosure provides, a method of treating osteoarthritis in a subject in need thereof, the method comprising administering to the subject a therapeutically effective amount of a USP16 inhibitor. In some cases, treating osteoarthritis comprises altering an osteoarthritis marker. In some cases, the osteoarthritis marker is selected from a senescent marker (including, but not limited to, SA-β-gal, CDKN2D, CDKN2A, CDKN1B, CDKN1A, gamma-H2Ax), mitochondrial reactive oxygen species (ROS), cellular ROS, mitochondrial membrane potential, cartilage matrix degradation (including, but not limited to, MMPP13, MMP1, MMP3, ADAM8, ADAM9, ADAM21, ADAMTS3, ADAMTS15, ADAMTS17, TIMP4, SERPINA1), cartilage matrix deposition (including but not limited to, ACAN, COL2A, COL17A, COL28A1, COL10A, RUNX1, RUNX2), apoptosis (including, but not limited to, Caspase-6, -10, -12, BCL2, BCL6, BIRC3, BAD), cell cycle genes (including, but not limited to, CCND2, CCNA2, CCNB2, CCNB1, TOP2A, MKI67, BUB1, BUB1B, CDK6, RRM2, E2F2, E2F1), chondrogenic potential and self-renewal (including, but not limited to, SOX-9, SOX-6, SOX-5, BIRC5, CENPU, BMP2, ALDH2, ALDH4a1), and inflammation (including, but not limited to, NF-kB, p105 and p65 phosphorylation, IKK, IL-1RA IL-1β, IL-6, IL-8, TNFa, IL-17, CCL5, CCR1, CCR2. CCR3, CCR5, MCP1, COX2, PGE2, CX3CL1, IL23a, TNF).

In some cases, treating osteoarthritis comprises increasing expression of an osteoarthritis marker selected from ACAN, COL2a and SOX-9. In some cases, treating osteoarthritis comprises increasing staining in a Safranin-O or Toluidine Blue assay. In some cases, treating osteoarthritis comprises decreasing expression of an osteoarthritis marker selected from MMP-1, MMP-3, MMP-13, CDKN2A, CDKN1A, CDKN2D and SA-3-gal. In some cases, treating osteoarthritis comprises decreasing expression of inflammation markers, including, but not limited to, NF-kB, p105 and p65 phosphorylation, IKK, IL-1RA, IL-1β, IL-6, IL-8, TNFa, IL-17, CCL5, CCR1, CCR2. CCR3, CCR5, MCP1, COX2, PGE2, CX3CL1, IL23a, TNF). In some cases, treating osteoarthritis comprises increasing the expression of a stem cell marker including SOX-9 and ALDH2. In some cases, treating osteoarthritis comprises increasing H2AK119/H2AK118 ubiquitination or modulating H3K27me3. In some cases, the osteoarthritis marker is assessed in cells biopsied from an affected joint of the subject, in extracellular matrix biopsied from the affected joint of the subject, in synovial fluid, in blood, or in plasma.

In some cases, treating osteoarthritis comprises reversing or attenuating cartilage damage. In some cases, treating osteoarthritis comprises increasing cartilage thickness in a joint. In some cases, treating osteoarthritis comprises decreasing pain in an affected joint of the subject. In some cases, treating osteoarthritis comprises increasing the joint space or reducing the join space narrowing. In some cases, treating osteoarthritis comprises decreasing swelling or inflammation in an affected joint of the subject. In some cases, treating osteoarthritis comprises increasing mitochondrial membrane potential.

In some cases, treating osteoarthritis comprises decreasing mitochondrial ROS or cellular ROS. In some cases, treating osteoarthritis comprises decreasing cartilage matrix degradation. In some cases, treating osteoarthritis comprises improving an OARSI score of a joint. In some cases, treating osteoarthritis comprises improving a WOMAC score. In some cases, the USP16 inhibitor increases matrix deposition by chondrocytes.

In some cases, the osteoarthritis is injury-induced osteoarthritis, age-induced osteoarthritis, diabetes-induced osteoarthritis, familial osteoarthritis, or idiopathic osteoarthritis. In some cases, the USP16 inhibitor decreases markers of aging. In some cases, the USP16 inhibitor increases markers of self-renewal.

In some cases, the subject is a mammal. In some cases, the mammal is a human, a dog, or a horse. In some cases, the USP16 inhibitor is administered by intra-articular injection.

In some embodiments the present disclosure provides, a method of treating a disease in a subject in need thereof, the method comprising contacting a mesenchymal stem cell (MSC) with a USP16 inhibitor and administering the MSC to the subject. In some cases, the MSC is an autologous MSC. In some cases, the MSC is an allogenic MSC. In some cases, the MSC is extracted from bone marrow, adipose tissue, umbilical cord blood or dental pulp. In some cases, the MSC is genetically modified prior to administering the MSC to the subject. In some cases, the genetic modification alters a SNP or alters the expression of a gene.

In some cases, the disease is acute renal failure, myocardial infarction, type I diabetes mellitus, type II diabetes mellitus, graft-versus-host disease, systemic lupus erythematosus, acute disseminated encephalomyelitis (multiple sclerosis), osteoarthritis, pulmonary fibrosis, osteogenesis imperfecta, metachromatic leukodystrophy (MILD) and Hurler syndrome (MPS-IH), amyotrophic lateral sclerosis, ulcerative colitis, Crohn's disease or articular cartilage defects. In some cases, administering the MSCs comprises intravenous infusion; intramyocardial transplantation, intravenous co-infusion with bone marrow transplant, intraocular administration or intra-articular injection.

In some embodiments the present disclosure provides, a method of protecting chondrogenic potential or self-renewal in mesenchymal stem cells, the method comprising contacting the mesenchymal stem cells with an effective amount of a USP16 inhibitor. In some cases, the mesenchymal stem cell is in the body of a mammal. In some cases, the mesenchymal stem cells are in, or proximal to, a joint of the mammal. In some cases, the mesenchymal stem cells are in culture. In some cases, the mesenchymal stem cells are expanded or selected in vitro and injected in subjects.

In some embodiments the present disclosure provides, a method of increasing cartilage production or proliferation of a chondrocyte or inhibiting senescence in a chondrocyte, the method comprising contacting the chondrocyte with an effective amount of a USP16 inhibitor. In some cases, the chondrocyte is in the body of a mammal. In some cases, the chondrocyte is in, or proximal to, a joint of the mammal. In some cases, the chondrocytes are in culture. In some cases, the chondrocytes are expanded or selected in vitro for autologous chondrocyte implantation (ACI) or matrix-assisted ACI (MACI) treatments.

In some cases, the USP16 inhibitor is a nucleic acid, a protein, or a small molecule. In some cases, the USP16 inhibitor is a small molecule. In some cases, the USP16 inhibitor is an RNAi molecule. In some cases, the RNAi molecule is an shRNA, an siRNA, a microRNA, or an asymmetric interfering RNA. In some cases, the USP16 inhibitor is antisense molecule, a lhRNA, an miRNA embedded shRNA, or a small internally segmented RNA. In some cases, the USP16 inhibitor is administered via a liposome or a nanoparticle.

In some cases, the USP16 inhibitor is administered via a viral vector. In some cases, the viral vector is selected from a retroviral vector, an adenoviral vector, and an adeno-associated viral vector. In some cases, the retroviral vector is a lentiviral vector. In some cases, the adenovirus is a helper-dependent adenovirus. In some cases, the adenovirus is a serotype 2 adeno-associated virus vectors (rAAV2) or a serotype 2.5 adeno-associated virus vectors (rAAV2.5) or self-complementary AAV (scAAV).

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1C illustrates the negative correlation between USP16 and SOX9 expression levels from human osteoarthritic patients (in silico data from dataset GSE55235). FIG. 1D illustrates the positive correlation of USP16 with MMP-3 expression levels from human osteoarthritic patients (in silico data from dataset GSE55235. FIG. 1E illustrates the positive correlation of USP16 with CDKN2A expression levels from human osteoarthritic patients (in silico data from dataset GSE55235

FIG. 3A illustrates cellular ROS measured using CM-H2DCFDA (General Oxidative Stress Indicator) and represented as % change of control. FIG. 3B illustrates mitochondrial ROS measured using MitoSOX and represented as % change of control. FIG. 3C illustrates mitochondrial membrane potential measured using JC-1 and represented as fold change of control. ON TARGETplus siRNA control or targeting USP16 (100 nM) was transfected in 3 OA patient chondrocytes and compared with 3 age-matched healthy controls, in 3 technical replicates at passage 2. Probability was determined by one-way ANOVA and Holm-Sidak's test for multiple comparisons between each treatment group. All data are shown as the mean±SEM and p values are indicated.

FIG. 4E illustrates Safranin-O staining for cartilage matrix degradation after 10 days culture. ON TARGETplus siRNA for USP16 (100 nM) was transfected in OA patient chondrocytes and compared with 3 age-matched healthy controls. Probability was determined by one-way ANOVA and Holm-Sidak's test for multiple comparisons between each treatment group. All data are shown as the mean±SEM and p values are indicated.

FIG. 5B illustrates the number of differentially expressed genes (DEG) in human OA- and HD-derived chondrocytes transfected with siRNA control or siUSP16. The DEG are compared to HD transfected with siRNA Control. ON TARGETplus siRNA control or targeting USP16 (100 nM) was transfected into chondrocytes at passage 2.

FIG. 6A shows qRT-PCR analysis of USP16 mRNA level in primary human bone marrow derived mesenchymal stem cells (MSCs) stimulated with IL13 (50 ng/ml) for 24 hrs. (con=MSC treated with siRNA control; siRNA=MSC treated with siRNA targeting USP16). Probability was determined by one-way ANOVA and Holm-Sidak's test for multiple comparisons between each treatment group. All data are shown as the mean±SEM and p values are indicated.

FIG. 6B illustrates Mitochondrial ROS measured using MitoSOX and represented as a % change of control. Probability was determined by one-way ANOVA and Holm-Sidak's test for multiple comparisons between each treatment group. All data are shown as the mean±SEM and p values are indicated.

FIGS. 6C-6E illustrate qRT-PCR analysis of SOX-9 (FIG. 6C), ACAN (FIG. 6D), and COL2A (FIG. 6E) mRNA level in primary human bone marrow derived MSCs stimulated with IL1β (50 ng/ml) for 24 hrs. Probability was determined by one-way ANOVA and Holm-Sidak's test for multiple comparisons between each treatment group. All data are shown as the mean±SEM and p values are indicated.

FIG. 15A shows representative images of toluidine blue staining of the joint of a MMT rat treated with AAV control (MMT-scramble) or AAV targeting USP16 (MMT-sh-USP16) 28 days post-surgery. The cumulative histopathology score of the tibia is shown in FIG. 15B. Probability was determined by one-way ANOVA and Holm-Sidak's test for multiple comparisons between each treatment group. All data are shown as the mean±SEM and p values are indicated.

DETAILED DESCRIPTION OF THE INVENTION

Figure 1B:
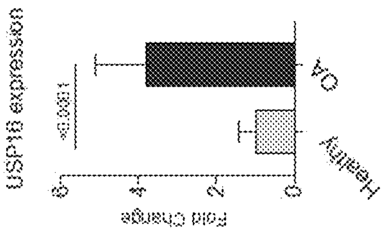
FIG. 1B illustrates the increase of USP16 expression by quantitative reverse transcriptase polymerase chain reaction (qRT-PCR) in primary articular chondrocytes from OA patients compared to age-matched healthy donors. N=3, 3 technical replicates were conducted as passage 2, cells were cultured for 10 days.

Osteoarthritis (OA) is a degenerative disease of the joints caused by cartilage erosion and it leads to great physical limitation, including difficulty of walking and standing. It is the most common joint disorder in the United States and symptomatic knee OA occurs in 10% men and 13% in women aged 60 years or older. Osteoarthritis may result from failure of chondrocytes to maintain homeostasis between synthesis and degradation of the extracellular matrix components, and/or due from dysfunction of mesenchymal stem cells preventing repair and renewal of the joint. Due in part to the poor self-healing capacity of articular cartilage and lack of specific diagnostic biomarkers, OA is a challenging disease with limited treatment options. While the traditional pharmacologic therapies such as non-steroidal anti-inflammatory drugs, corticosteroids and opioids are effective in relieving pain, they are incapable of reversing cartilage damage. The present disclosure provides disease-modifying osteoarthritis drugs (DMOAD) which may act on the key tissues involved in OA to prevent structural progression and therefore improve symptoms and patient reported quality of life outcomes.

Osteoarthritis (OA) is the most common form of arthritis and may be caused by mechanical wear and tear on joints. It usually begins later in life, with slow progression over years. OA is not an autoimmune disease.

There are currently no disease-modifying osteoarthritis drug (DMOAD) that could inhibit the structural disease progression of OA and improve symptoms and/or function. Moreover, DMOAD will probably differ from disease modifying drugs useful for autoimmune joint diseases since the underlying disease etiologies are different.

USP16 is a deubiquitinase (DUB) enzyme that removes ubiquitin from histone H2A on lysine 119, a critical mark for the maintenance of multiple somatic tissues. USP16 is a stem cell regulator in multiple tissues in human and mouse models, and a reduction in levels of USP16 resulted in an expansion of the stem cell compartment in bone marrow, brain, breast and primary fibroblasts.

Osteoarthritis is a complex disease characterized by an increase of senescent cells (SA-β-Gal) and a reduction of stem cell functions (SOX-9), proportionate to the progression of the disease. USP16 expression is highly upregulated in osteoarthritis (OA) chondrocytes and synovial tissues. Moreover, the genetic locus of USP16 contains a SNP (rs6516886) strongly associated with familial OA. Genetic downregulation of USP16 in patient-derived articular chondrocytes promotes cellular and mitochondrial health and reduces senescence associated markers, like SA-3-gal and CDKN2A. Furthermore, USP16 knockdown in human bone marrow-derived mesenchymal stem cells increased SOX-9 levels, promoted chondrogenic potential, and increased matrix deposition.

This disclosure provides methods of treating osteoarthritis in a subject in need thereof, the methods comprising administering to the subject a therapeutically effective amount of a USP16 inhibitor. Treating osteoarthritis may comprise altering an osteoarthritis marker. Examples of osteoarthritis markers include, but are not limited to: senescent markers (including, but not limited to, SA-β-gal, CDKN2D, CDKN2A, CDKN1B, gamma-H2Ax), mitochondrial ROS, cellular ROS, mitochondrial membrane potential, cartilage matrix degradation (including, but not limited to, MMP13, MMP1, MMP3, ADAM8, ADAM9, ADAM21, ADAMTS3, ADAMTS15, ADAMTS17, TIMP4, SERPINA1), cartilage matrix deposition (including but not limited ACAN, COL2A, COL17A, COL28A1, COL10A, RUNX1, RUNX2), apoptosis (including, but not limited to, Caspase-6, -10, -12, BCL2, BCL6, BIRC3, BAD), cell cycle genes (including, but not limited to, CCND2, CCNA2, CCNB2, CCNB1, TOP2A, MKI67, BUB1, BUB1B, CDK6, RRM2, E2F2, E2F1), chondrogenic potential and self-renewal (including, but not limited to, SOX-9, SOX-6, SOX-5, BIRC5, CENPU, BMP2, ALDH2, ALDH4a1), and inflammation (including, but not limited to, NF-kB, p105 and p65 phosphorylation, IKK, IL-1Ra, IL-1β, IL-6, IL-8, TNFa, IL-17, CCL5, CCR1, CCR2. CCR3, CCR5, MCP1, COX2, PGE2, CX3CL1, IL23a, TNF).

Treating osteoarthritis may comprise increasing expression of an osteoarthritis marker selected from ACAN, COL2A and SOX-9. Treating osteoarthritis may comprise increasing cartilage production; which may be represented by increasing staining in a Safranin-O or Toluidine Blue assay. In some cases, treating osteoarthritis comprises decreasing expression of an osteoarthritis marker selected from MMP-1, MMP-3, MMP-13, CDKN2A, CDKN1A, CDKN2D and SA-3-gal. In further cases, treating osteoarthritis comprises decreasing expression of an inflammation marker, including, but not limited to, IL-1β, IL-6, IL-8, TNFa, IL-17, CCL5, CCR1, CCR2, CCR3, CCR5, MCP1, COX2, PGE2. Treating osteoarthritis may comprise increasing the expression of a stem cell marker, such as SOX-9 and ALDH2.

The osteoarthritis marker may be assessed in any patient biopsy. For example, cells biopsied from an affected joint of the subject, in extracellular matrix biopsied from the affected joint of the subject, in synovial fluid, in blood, or in plasma.

In some embodiments, treating osteoarthritis comprises reversing or attenuating cartilage damage. Treating osteoarthritis may comprise increasing cartilage thickness or decreasing its degeneration in a joint, increasing the joint space or reducing the join space narrowing, decreasing pain in an affected joint of the subject, and/or decreasing swelling or inflammation in an affected joint of the subject. At a cellular level treating osteoarthritis may comprise restoring a ‘healthy’ expression profile in a chondrocyte or MSC. Treating osteoarthritis may also comprise decreasing senescence of chondrocytes and/or MSCs, or increasing self-renewal of MSCs. At a cellular level treating osteoarthritis may comprise increasing mitochondrial membrane potential and/or decreasing mitochondrial ROS, cellular ROS, cartilage matrix degradation or reducing inflammation. Treating osteoarthritis may comprise improving an OARSI score of a joint or a WOMAC score.

In some cases, the USP16 inhibitor may promote chondrogenic potential of mesenchymal stem cells and/or increase matrix deposition by chondrocytes. The USP16 inhibitor may decrease markers of aging or increase markers of self-renewal.

The subject may be a mammal, for example a human, a dog, or a horse. In some cases, the subject may have an injury induced osteoarthritis. In some cases, the subject may have osteoarthritis or a family history of osteoarthritis.

The subject may have osteoarthritis or may have a family history of osteoarthritis. The subject may be a carrier for a SNP which may increase the risk of developing osteoarthritis, or which may increase the efficacy of a USP16 inhibitor treatment. The subject may have a SNP rs6516886.

The present disclosure also provides methods of protecting self-renewal capabilities and/or chondrogenic potential in mesenchymal stem cells exposed to an inflammatory cytokine, the methods comprising contacting the mesenchymal stem cells with an effective amount of a USP16 inhibitor. The mesenchymal stem cell may be in the body of a mammal, for example a subject. In some cases, the mesenchymal stem cells are in, or proximal to, a joint of the mammal. In other cases, the mesenchymal stem cells may be in culture. MSCs can be extracted, isolated and derived from a variety of autologous and allogenic (from a healthy donor) locations such as bone marrow (BM-MSC), adipose tissue (ADMSC), umbilical cord blood and dental pulp. MSCs can be isolated and directly injected intra-articularly or can undergo in vitro expansion prior to the injection in patients. The MSCs may be administered to the subject after exposure to the USP16 inhibitor. In some cases, the MSCs may be genetically modified, to alter expression of USP16 or another gene, prior to administration to the subject. The methods may protect self-renewal abilities and chondrogenic potential in mesenchymal stem cells when reinjected into the patients and thus increase its therapeutic benefit. Indeed, the inflammatory microenvironment (tumor necrosis factor (TNF)-α, interleukin (IL)-1, IL-6, IL-2, IL-7, IL-15, or IL-21) in the OA joint drives MSCs dysfunction. The USP-16 inhibitor treated MSCs may be administered to a subject to treat a disease or a disorder, for example an autoimmune disease (including, but not limited to, rheumatoid arthritis or systemic lupus erythematous), a cancer (including, but not limited to, advanced gastrointestinal cancer or metastases solid tumors), a cardiac disorder (including, but not limited to, acute myocardial infarction, chronic heart failure, class 2 or 3 heart failure, or ischemic stroke), graft vs host disease (GvHD, including, but not limited to, chronic GvHD, acute GvHD, Grades B-D acute GvHD), an inflammatory bowel disease (including, but not limited to, Crohn’s disease or ulcerative colitis), kidney disorders (including, but not limited to, acute kidney injury diabetic nephropathy, liver/kidney failure or renal transplantation), or a neurodegenerative disease (including, but not limited to, ALS, chronic progressive multiple sclerosis, degenerative disc disease, or multiple sclerosis).

The present disclosure provides a method of treating a disease in a subject in need thereof, the method comprising contacting an MSC with a USP16 inhibitor and administering the MSC to the subject. The present disclosure also provides a method of treating a disease or disorder in a subject, the method comprising exposing a plurality of MSCs to a USP16 inhibitor in vitro and administering the plurality of exposed MSCs to the subject. The disease or disorder may be an autoimmune disease (including, but not limited to, rheumatoid arthritis or systemic lupus erythematous), a cancer (including, but not limited to, advanced gastrointestinal cancer or metastases solid tumors), a cardiac disorder (including, but not limited to, acute myocardial infarction, chronic heart failure, class 2 or 3 heart failure, or ischemic stroke), graft vs host disease (GvHD, including, but not limited to, chronic GvHD, acute GvHD, Grades B-D acute GvHD), an inflammatory bowel disease (including, but not limited to, Crohn's disease or ulcerative colitis), kidney disorders (including, but not limited to, acute kidney injury diabetic nephropathy, liver/kidney failure or renal transplantation), or a neurodegenerative disease (including, but not limited to, ALS, chronic progressive multiple sclerosis, degenerative disc disease, or multiple sclerosis). The MSCs may be autologous or allogenic and may be extracted from many locations such as bone marrow (BM-MSC), adipose tissue (ADMSC), umbilical cord blood and dental pulp. MSCs can be isolated and directly administered to the subject or can undergo in vitro expansion prior to the injection in patients. In some cases, the MSCs may be genetically modified, to alter expression of USP16 or another gene, prior to administration to the subject.

The present disclosure also provides methods of increasing cartilage production and cell health in a chondrocyte, the methods comprising contacting the chondrocyte with an effective amount of a USP16 inhibitor. The chondrocyte may in the body of a mammal, for example, in or proximal to a joint of the mammal. In other cases, the chondrocytes can be cultured in vitro and used for autologous chondrocyte implantation (ACI) or matrix-assisted ACI (MACI) treatments. ACI and MACI are established techniques for the treatment of ulcerated cartilage and cartilage defects. It involves an initial cartilage biopsy, from which chondrocytes are cultured in vitro. In a second surgical procedure, a flap or membrane is then sutured (or glued) over the defect and the cultured chondrocytes are injected under this barrier. The chondrocytes may be administered to the subject after exposure to the USP16 inhibitor to increase their cell health, proliferation and cartilage deposition abilities and to delay senescence. In some cases, the chondrocytes may be genetically modified, to alter expression of USP16 or another gene, prior to administration to the subject.

USP16 Inhibitors

Provided herein are inhibitors of USP16. Such inhibitors may reduce the expression and/or activity of USP16 in a cell. Exemplary inhibitors of USP16 include, for example, nucleic acids, proteins, small molecules, or large molecules. Small molecule inhibitors of USP16 may be identified using a biochemical assay testing the enzymatic activity of recombinant human USP16.

In some embodiments, the inhibitor of USP16 is an RNA-guided nuclease, such as a Cas nuclease, or a nucleic acid encoding the same. In some embodiments, the Cas nuclease is a Cas9 nuclease, a Cas12(a) nuclease (Cpf1), a Cas12b nuclease, a Cas12c nuclease, a TrpB-like nuclease, a Cas13a nuclease (C2c2), a Cas13b nuclease, a Cas14 nuclease, a CasX nuclease, a CasY nuclease, or modified or truncated variants thereof. In some embodiments, the Cas9 nuclease is isolated or derived from *S. pyogenes* or *S. aureus*. Cas nucleases bind to a guide RNA (e.g., a single-molecule or dual-molecule gRNA), which binds to a target nucleic acid sequence. Single-molecule gRNAs (e.g., sgRNAs) typically comprise a spacer sequence that is complimentary to a target DNA sequence of interest, and a scaffold sequence that binds to the Cas nuclease. In some embodiments, the spacer sequence targets a specific site in the USP16 gene, such as an intron or an exon of the USP16 gene. In some embodiments, the spacer sequence targets non-coding regions, including, but not limited to, a promoter, an enhancer, or other untranslated regions (e.g. 5'UTR or 3'UTR) of the USP16 gene.

In some embodiments, an RNA guided nuclease, such as Cas9, and a ssDNA template is used to alter a genetic sequence to inhibit USP16. For example, an RNA guided nuclease and a ssDNA template may be used to alter a SNP. In some cases, the USP16 inhibitor is a Cas9 protein, a guide RNA specific for SNP rs6516886, and a ssDNA template to alter the OA-risk T nucleotide of the SNP.

In some embodiments, the inhibitor of USP16 is a transcription activator-like effector nuclease (TAL nuclease), or one or more nucleic acids encoding the same. A TAL nuclease may comprise a TAL effector DNA-binding domain fused to a DNA cleavage domain. The TAL nuclease may target the USP16 gene, such as in intron or an exon of the USP16 gene. In some embodiments, the TAL nuclease targets non-coding regions, including, but not limited to, a promoter, an enhancer, or other untranslated regions (e.g. 5'UTR or 3'UTR) of the USP16 gene.

In some embodiments, the inhibitor of USP16 is a zinc (Zn) finger nuclease, or one or more nucleic acids encoding the same. A Zn finger nuclease may comprise a zinc finger DNA-binding domain fused to a DNA cleavage domain (e.g., FokI or a variant thereof). The Zn finger nuclease may target the USP16 gene, such as in intron or an exon of the USP16 gene. In some embodiments, the Zn finger nuclease targets non-coding regions, including, but not limited to, a promoter, an enhancer, or other untranslated regions (e.g. 5'UTR or 3'UTR) of the USP16 gene.

In some embodiments, the inhibitor is a RNAi molecule. For example, the inhibitor may be a small hairpin RNA (shRNA), a small interfering RNA (siRNA), a microRNA, or an asymmetric interfering RNA. In some embodiments, the inhibitor is a shRNA targeting a sequence of the USP16 gene. In some embodiments, the inhibitor is a shRNA targeting the following sequence of the USP16 gene: 5'-TCCAGAAGGAATATCACTT-3' (SEQ ID NO: 6, 5'-GACTGTAAGACTGACAATAAA-3' (SEQ ID NO: 7) and 5'-TATATCAGTTCACCCGTAAT-3' (SEQ ID NO: 8) or a sequence at least 90%, at least 95%, at least 96%, at least 97%, at least 98%, or at least 99% identical thereto. In some embodiments, the inhibitor is an siRNA targeting the following sequences of the USP16 gene: Usp16-1, 5'-GCCUAUGCCAAGGCAAGAA-3'; Usp16-2, 5'-CCUCCUGUUCUUACUCUUCAUUUAA-3'; Usp16-3, 5'-CCGGAAAUCUUAGAUUUGGCUCCUU-3'; Usp16-4, 5'-GGAUAAUGAUCUGGAGGUU-3'; Usp16-5, 5'-GAAUGAUAGUCAUACUCCU-3' or other variants.

In some embodiments, the inhibitor of USP16 is selected from an antisense molecule, a phosphorothioate oligonucleotide, a DNA-RNA chimera, a morpholino oligo, a lhRNA, a miRNA embedded shRNA, a small internally segmented RNA, an antibody, and an exosome.

In some embodiments, USP16 inhibition refers to knockdown of USP16 expression (also interchangeably referred to herein as downregulation, decreasing, silencing, etc. of expression). The knockdown need not be a total knockout of expression, and so in some embodiments, the inhibitor of USP16 may reduce expression of USP16 by at least 10%, at least 20%, at least 30%, at least 40%, at least 50%, at least 60%, at least 70%, at least 80%, at least 90%, at least 95%, or at least 99%. In some embodiments, the inhibitor of USP16 may completely eliminate expression of USP16 (e.g. knockout).

In some embodiments, USP16 inhibition refers to knockdown of USP16 activity (also interchangeably referred to herein as downregulation, decreasing, silencing, etc. of activity). In some embodiments, the inhibitor of USP16 may reduce activity of USP16 by at least 10%, at least 20%, at least 30%, at least 40%, at least 50%, at least 60%, at least 70%, at least 80%, at least 90%, at least 95%, or at least 99%. In some embodiments, the inhibitor of USP16 may completely eliminate the activity of USP16.

In some embodiments, USP16 inhibition refers to a modification of the USP16 gene, which renders it inoperative (e.g., a knockout of the USP16 gene or specific base mutations (e.g. mutations in the catalytic site).

In some embodiments, after a USP16 inhibitor is contacted with cells, USP16 expression and/or activity is inhibited in at least 10%, at least 20%, at least 30%, at least 40%, at least 50%, at least 60%, at least 70%, at least 80%, at least 90%, at least 95%, at least 99%, or 100% of the cells.

Delivery to Cells

The USP16 inhibitor may be delivered to a cell in numerous different ways. For example, the inhibitor (e.g., a small molecule) may be added directly to the media of the cell in culture. In some embodiments, the inhibitor may be delivered to the cell using a vector.

In some embodiments, the inhibitor may be delivered to the cell using a non-viral vector. Exemplary non-viral vectors include, but are not limited to, nanoparticles (e.g., polymeric nanoparticles), liposomes (e.g., cationic liposomes), cationic lipid-DNA complexes, lipid emulsions, calcium phosphate, polymer complexes, or combinations thereof. The non-viral vector may be used to package a double stranded DNA (dsDNA) (e.g., a plasmid), or a single stranded DNA (ssDNA). In some embodiments, non-viral vector may comprise a plasmid comprising a sequence encoding an inhibitor of USP16.

In some embodiments, the inhibitor may be delivered to the cell using a viral vector. For example, a nucleic acid sequence encoding the inhibitor may be packaged into a viral vector, and the viral vector may be subsequently used to transduce the cell. In some embodiments, the viral vectors of the instant disclosure are replication defective, or at least conditionally replication defective. Suitable viral vectors for use in the compositions and methods of the disclosure include, but are not limited to, retroviral vectors (e.g., lentiviral vectors), adenoviral vectors, and adeno-associated viral vectors (AAVs). In some cases, the viral vector is a helper-dependent adenovirus. In some embodiments, the viral vector is an AAV vector having a serotype selected from AAV1, AAV2, AAV2.5, AAV3, AAV4, AAV5, AAV6, AAV7, AAV8, AAV9, AAV10, AAV11, AAV12, AAVrh.8, AAVrh.10, AAVrh32.33, AAVrh74, bovine AAV, self-complementary AAV (scAAV) and avian AAV.

Pharmaceutical Compositions

Also provided are pharmaceutical compositions comprising an inhibitor of USP16. In some embodiments, a pharmaceutically acceptable composition comprises an inhibitor of USP16 and one or more of a pharmaceutically acceptable carrier or excipient.

As used herein, "pharmaceutically acceptable carrier" or "pharmaceutical acceptable excipient" includes any material which, when combined with an inhibitor of USP16, allows the inhibitor of USP16 to retain biological activity. An excipient can give form or consistency, or act as a diluent. Suitable excipients include but are not limited to stabilizing agents, wetting and emulsifying agents, salts for varying osmolarity, encapsulating agents, buffers, and skin penetration enhancers. Examples include, but are not limited to, any of the standard pharmaceutical carriers/excipients such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers may be formulated by conventional methods (see, for example, Remington's Pharmaceutical Sciences, 18th edition, A. Gennaro, ed., Mack Publishing Co., Easton, PA, 1990; and Remington, The Science and Practice of Pharmacy 21st Ed. Mack Publishing, 2005).

Methods of Treating

In some embodiments, a method of treating a subject in need thereof may comprise administering to the subject a therapeutically effective amount of an inhibitor of USP16. As used herein, the term "therapeutically effective amount" means the amount of an inhibitor that is sufficient to reduce the expression and/or activity of USP16 in a subject or in a cell.

In some embodiments, a method of treating a subject in need thereof may comprise administering to the subject a vector (e.g., a viral vector) comprising a sequence encoding an inhibitor of USP16. The viral vector may inhibit USP16 in one or more cell types in the subject in vivo. The vector could be an adeno-associated vector of different serotypes. (e.g. AAV-2, HIDAd)

A USP16 inhibitor or a cell modified to downregulate USP16 or a cell previously exposed a therapeutically effective amount of an inhibitor of USP16 may be administered to the subject using various different administration routes, including oral, rectal, transmucosal, topical, transdermal, inhalation, intravenous, subcutaneous, intradermal, intramuscular, intra-articular, intrathecal, intraventricular, intravenous, intraperitoneal, intranasal, or intraocular routes of administration. The USP16 inhibitor or a cell modified to downregulate USP16 or a cell previously exposed a therapeutically effective amount of an inhibitor of USP16 may be administered by intra-articular injection. In some cases, cells may be removed from a subject, treated with a USP16 inhibitor and administered back to the subject.

EXAMPLES

Example 1: USP16 is Upregulated in OA Joints and OA-Derived Chondrocytes

Figure 1A:
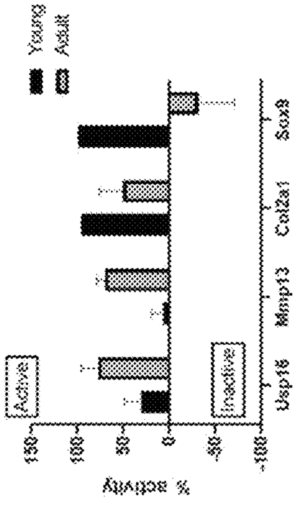
FIG. 1A illustrates gene expression levels for USP16, MMP13, Col2A1, SOX-9 from young and adult mice joints from the dataset GSE151303. Aging induces USP16 expression and other markers associated to OA, such as an increase in MMP13 and COL2A1 and a decrease in SOX-9.

In silico analysis of mouse RNA expression data from young and adult mice joints from the dataset GSE151303 showed increased expression of USP16 and MMP13 in the aged joints, and decreased expression of Col2a1 and Sox9 (FIG. 1A). Gene profiles were normalized against common reference. Each gene expression was transformed to percentile and ranked using −100% to +100% on the basis of its value relative to the reference. Aging induces USP16 expression and other markers associated to OA, such as an increase in MMP13 and a decrease in Sox-9.

RNA levels of human healthy and OA-derived chondrocytes cultured in vitro show that USP16 expression is significantly higher in OA-derived chondrocytes compared to the healthy controls (FIG. 1B). Briefly, human articular chondrocytes (HAC) from osteoarthritic (OA) affected individuals and age-matched healthy donors were obtained from Sigma-Aldrich (St. Louis, MO, USA), Articular Engineering and BioIVT. Chondrocytes were derived from the human articular cartilage of donors. Human chondrocytes were cultured in chondrocyte growth medium (PromoCell, Germany) supplemented with 10% fetal bovine serum (FBS) (Sigma-Aldrich), 1% penicillin-streptomycin (PS) (ThermoFisher Scientific, Waltham, MA). Cells were cultured for 10 days and RNA was isolated using the RNeasy Mini Kit (Qiagen). cDNA was synthesized using QuantaBio, and reverse transcription PCR was performed according to the manufacturer's instructions.

Figure 1C:
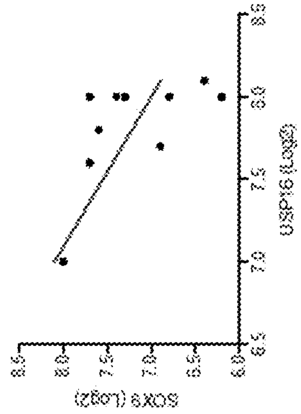
FIG. 1C-1E show the correlation of USP16 expression with markers of OA.
Figure 1D:
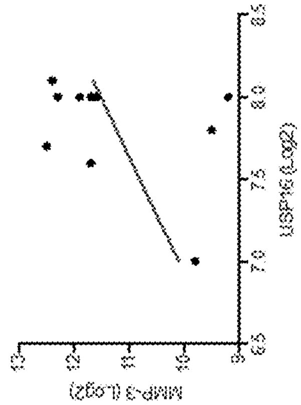
Figure 1E:
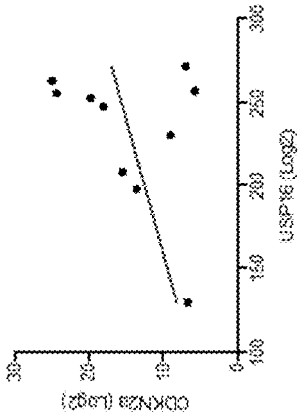

In silico analysis of human RNA expression data from dataset GSE55235 showed a negative correlation between USP16 and SOX-9 expression (FIG. 1C), the stem cell regulator of chondrogenesis, and a positive correlation with MMP-3 (FIG. 1D), a metalloprotease responsible for cartilage degradation and a strong biomarker of OA. A correlation was also observed for CDKN2A (FIG. 1E).

Example 2: USP16 Downregulation in HAC Delays Cellular Senescence

Figure 2A:
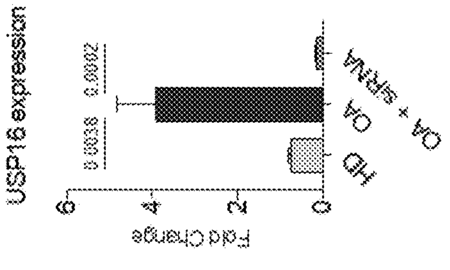
FIGS. 2A-2B illustrate the decrease in USP16 mRNA levels (FIG. 2A) and CDKN2A mRNA levels (FIG. 2B) in primary articular chondrocytes from healthy and OA patients cultured for 10 days upon USP16 downregulation. ON TARGETplus siRNA for USP16 (100 nM) was transfected in samples 3 OA patient chondrocytes and analyzed in 3 technical replicates at passage 2. Probability was determined by one-way ANOVA and Holm-Sidak's test for multiple comparisons between each treatment group. All data are shown as the mean±SEM and p values are indicated.
Figure 2B:
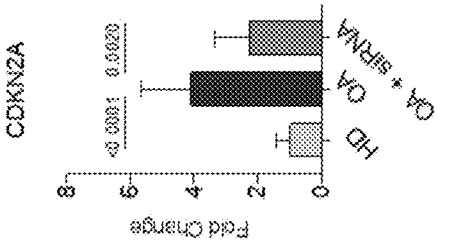
Figure 2C:
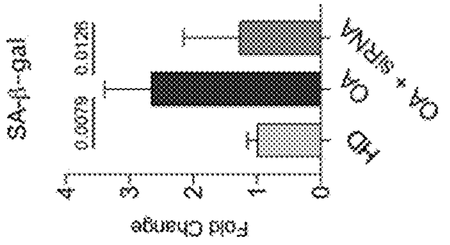
FIG. 2C illustrates reversion of SA-beta-GAL fluorescence intensity after cells were cultured for 10 days upon USP16 downregulation. ON TARGETplus siRNA for USP16 (100 nM) was transfected in 3 OA patient-derived chondrocytes and compared with 3 age-matched healthy controls, in 3 technical replicates at passage 2. Probability was determined by one-way ANOVA and Holm-Sidak's test for multiple comparisons between each treatment group. All data are shown as the mean±SEM and p values are indicated.

To interrogate the specific role of USP16 in OA, healthy and OA-derived articular chondrocytes were cultured in vitro for 10 days to exacerbate cellular stress. Under these conditions, we observed increased expression of OA-specific markers, such as SA-3-Gal, CDKN2A, ROS, MMPs and COL2A in AO-chondrocytes compared to healthy controls (FIGS. 2, 3 and 4). USP16 expression was then silenced by means of a siRNA in OA-derived chondrocytes (FIG. 2A) to evaluate the response of downstream pathways. siRNA was transfected to healthy control and patient-derived chondrocytes or MSCs using Lipofectamine® 2000 Transfection Reagent (Invitrogen) as using manufacture's protocols. CDKN2A gene expression was highly increased in OA chondrocytes compared to healthy controls and USP16 down regulation significantly reduced its mRNA expression (FIG. 2B). Further, when the SA-3-Gal activity was analyzed, the transient knockdown of USP16 was sufficient to block this activity to levels compared to heathy chondrocytes (FIG. 2C). These data show that USP16 targeting reduces the levels of CDKN2A expression and SA-3-Gal activity, leading to reduced cellular senescence.

Briefly, human articular chondrocytes (HAC) from OA and healthy age-match donors were obtained from commercial vendors and cultured in Chondrocyte Growth Medium (PromoCell). siRNA (control and targeting USP16) was transfected to healthy control and patient-derived chondrocytes using Lipofectamine® 2000 Transfection Reagent (Invitrogen) as suggested by the manufacture's protocols and RNA expression was assessed after 10 days. RNA was isolated from primary articular chondrocytes or MSCs using the RNeasy Mini Kit (Qiagen). cDNA was synthesized using qScript cDNA synthesis kit (Quantabio), and reverse transcription PCR was performed according to the manufacturer's instructions.

Figures 3A, 3B, 3C:
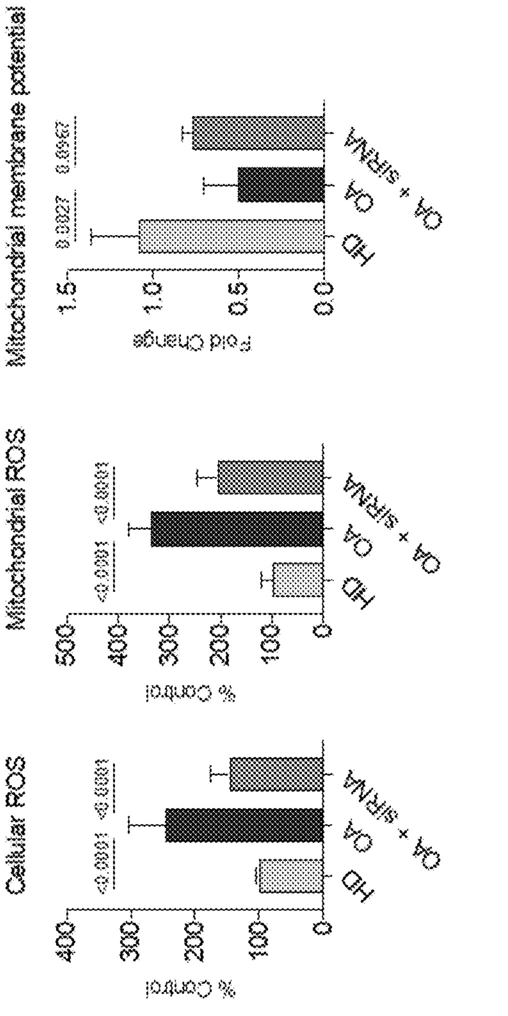
FIGS. 3A-3C illustrate that down regulation of USP16 reduces mitochondrial and cellular stress.

Example 3: USP16 Downregulation Mitigates the High Level of Cellular Stress Present in OA-Derived Chondrocytes ROS production and oxidative stress were elevated in articular chondrocytes isolated from patients with OA (FIG. 3A). Mitochondria in OA chondrocytes were also affected and contribute to mitochondrial specific ROS increase (FIG. 3B-C). Reducing USP16 expression in patient-derived OA chondrocytes positively impacted mitochondrial health as measured by mitochondrial ROS production and mitochondrial membrane potential and reducing overall ROS levels (FIG. 3).

For cellular ROS detection, cells were incubated with 2,7 dichloro-fluorescin diacetate (DCFDA) (Abcam) 100 μM for 30 min at 37° C. in the dark, and fluorescence was analyzed with excitation/emission at 495/529 nm, using SpectraMax M2e (Molecular devices). Fluorescence intensity was then normalized for cell number. To determine mitochondrial ROS production, cells were treated with 5 μM MitoSOX™ Red, a mitochondrial superoxide indicator (Invitrogen) for 10 min at 37° C., according to the manufacturer's protocol, and fluorescence was analyzed with excitation/emission at 510/580 nm, using SpectraMax M2e (Molecular devices).

For measurement of mitochondrial membrane potential cells were treated with 5 μM JC-1 (5,5',6,6'-tetrachloro-1, 1',3,3'-tetraethylbenzimidazolcarbocyanine iodide) dye (Invitrogen) in HBSS (Hank's balanced salt solution) together with DAPI (4',6-Diamidino-2-Phenylindole, Dihydrochloride) (Thermo Fisher) for 20 min at 37° C., and the fluorescence was analyzed with excitation/emission at 485/590 nm for mitochondrial polarization and at 485/525 nm for mitochondrial depolarization using SpectraMax M2e (Molecular devices). The mitochondrial depolarization was indicated by a decrease in ratio of polarization to depolarization.

Figure 4D:
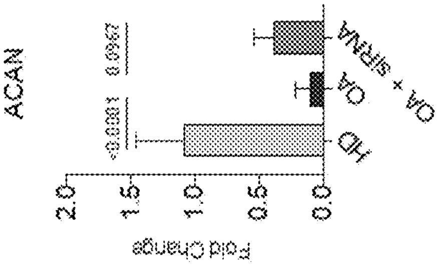
FIGS. 4A-4E illustrate that down regulation of USP16 reduces chondrocyte catabolism and increases extracellular matrix (ECM) deposition. qRT-PCR analysis of MMP-1 (FIG. 4A), MMP-3 (FIG. 4B), MMP-13 (FIG. 4C), and Aggrecan (ACAN, FIG. 4D) mRNA levels in primary articular chondrocytes from healthy and OA patients cultured for 10 days.
Figure 4C:
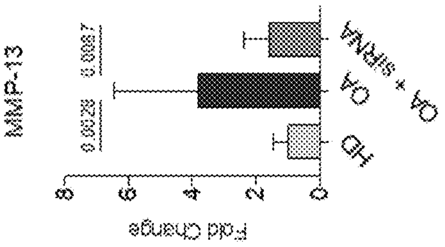
Figure 4B:
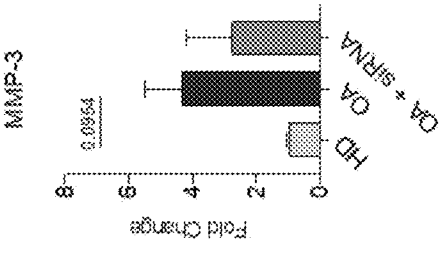
Figure 4A:
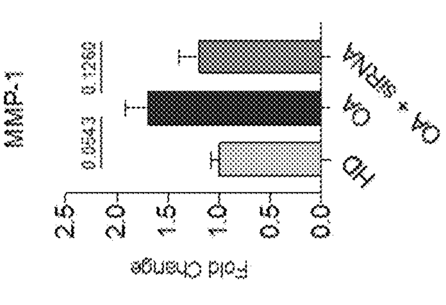
Figure 4E:
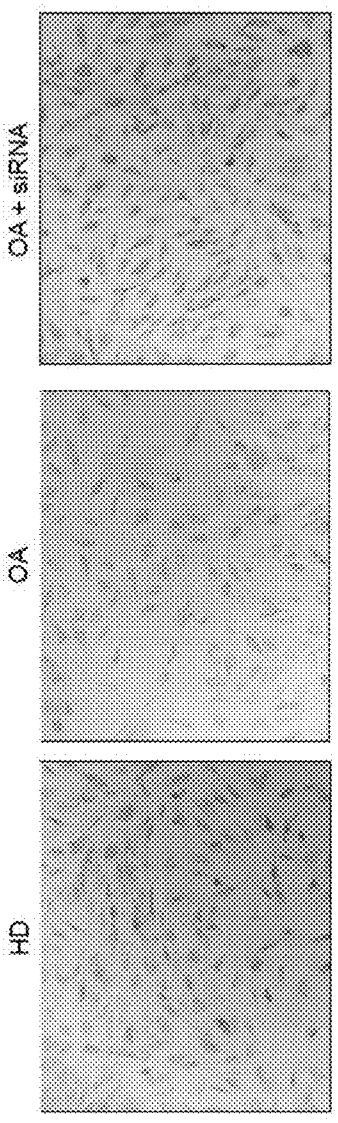

Example 4: USP16 Downregulation Restore Cartilage Deposition and Tissue Homeostasis in HAC Human OA-derived articular chondrocytes (HAC) were transiently transfected with a siRNA control or targeting USP16 as described in Example 2, and the cells were cultured in vitro for 10 day to exacerbate the OA-phenotype. OA-derived chondrocytes upregulated catabolic enzymes, resulting in reduced extracellular matrix deposition. USP16 transient knockdown (described in Example 2) rescued the increase in MMP-1, MMP-3 and MMP-13 gene expression in patient-derived OA chondrocytes (FIG. 4A-C). Furthermore, reducing USP16 gene expression in OA chondrocytes, increased mRNA levels of aggrecan (ACAN), a critical component for cartilage structure and the function of joints (FIG. 4D) as well as Safranin-O staining, which is proportional to the proteoglycan content in the cartilage tissue (FIG. 4E). After removal of the culture medium, the cells were fixed in 4% paraformaldehyde for 30 min, then washed twice with PBS before the addition of 0.1% stock solutions of safranin O. After 30 min incubation at room temperature, the dye solution was removed, and the cells were washed with distilled water. Human articular chondrocytes were stained after 10 days in culture as above.

These results suggest that the increase in USP16 levels observed in OA chondrocytes not only affects catabolism and cellular stress, but it also increases Extracellular Matrix (ECM) deposition. Most importantly, targeting USP16 expression in patient-derived chondrocytes not only blocked their progressive degeneration but also partially rescued their functionality.

Figure 5A:
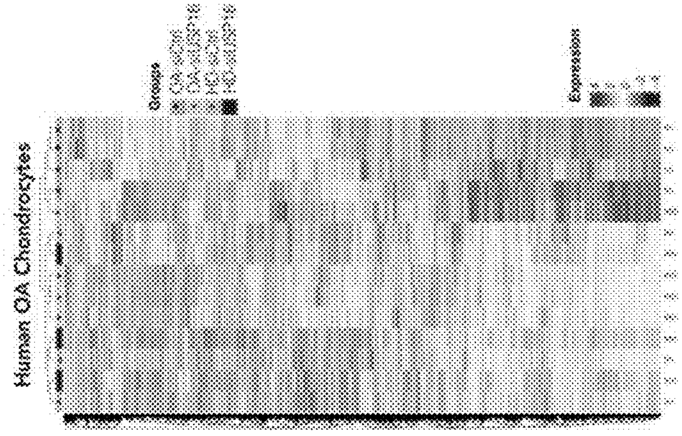
FIG. 5A-5B illustrate that USP16 downregulation normalizes the altered gene expression profile of OA-derived chondrocytes. A hierarchical clustering of genes differentially expressed in OA patient chondrocytes and age-matched healthy controls after transfection with siRNA control or targeting USP16. ON TARGETplus siRNA control or targeting USP16 (100 nM) was transfected into chondrocytes at passage 2.

Example 5: USP16 Transient Downregulation in HAC Partially Reverts OA Gene Signature To explore pathways regulated by USP16 in OA, RNA sequencing was performed on four independent chondrocyte lines derived from OA patients and healthy donors (HD) and transfected with siRNA control or siRNA USP16. The cells were harvested after 10 days and RNA sequencing was performed via Illumina platform. The levels of USP16 knockdown were verified at the moment of harvesting by qRT-PCR. The hierarchical cluster analysis (FIG. 5A) of the data provided by Novogene Co., Ldt demonstrate:

1. OA and HD created two separate clusters, with more than 6000 differentially expressed genes (DEG, $p<0.05$)
2. OA-derived chondrocytes downregulated for USP16 clustered with the HD samples rather than with the OA samples, meaning that gene expression was partially reverted to its "normal" state.

Figure 5B:
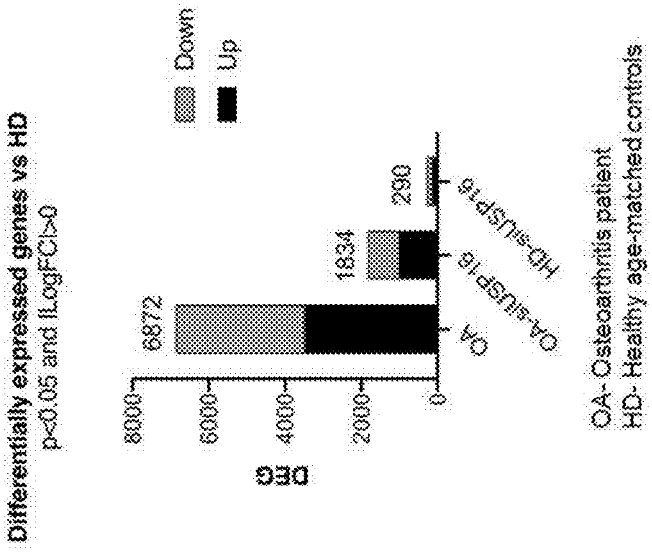

The number of statistically DEG (|LogFC|>0 and $p<0.05$) between OA and HD was normalized by 73% when USP16 was downregulated (FIG. 5B).

Example 6: USP16 Knockdown Rescues Stem Cell Properties and Dysfunction of Mesenchymal Stem Cells in an In Vitro Model of OA OA is a complex disease, where senescence and chondrocyte dysfunction may be accompanied by a decrease in stem cell activity and regeneration. In healthy cartilage, endogenous articular cartilage repair may be a native process of reconstructing damaged cartilage to original structure and function. Intra- and peri-articular mesenchymal stem/progenitor cells (MSCs) are believed to be the main drivers of endogenous articular cartilage repair, they have the ability to migrate from local or adjacent stem cell niches and exert their reparative capabilities in cartilage lesions. In OA, the regenerative capacity is be impaired also because of MSC scarcity, exhaustion and/or malfunction.

The role of USP16 was investigated in bone marrow-derived MSCs from healthy donors and cultivated under the inflammatory stimulus of IL1β, to mimic the OA niche. Interleukin-1 beta (IL-1β) is a key cytokine involved in the pathogenesis of OA, which may induce inflammatory reactions, and also independently prompt catabolic effects, which can block MSC chondrogenesis. Human bone marrow-derived MSCs were purchased from Sigma-Aldrich (St. Louis, MO, USA) and PromoCell. MSCs were subsequently cultured in MesenPRO RS medium (Invitrogen) supplemented with 1% penicillin/streptomycin and 2 mM glutamine. The medium was changed every 4-5 days until cells reached 70-80% confluency. Cells were then detached with 0.5% trypsin-EDTA (Sigma-Aldrich), counted and split into different tissue culture flasks and further cultured as already described. Cells were placed in a 37° C. humidified incubator containing 5% $CO_2$.

MSCs were transfected with siRNA control and targeting USP16, as described in Example 2; at a minimum of 90% confluence were washed twice with warm Dulbecco's phosphate-buffered saline (DPBS), and fresh media supplemented with 50 ng/ml IL-1β (Peprotech, 200-01B) was added. Cells were harvested 24 hrs post IL-1β induction.

Figure 6B:
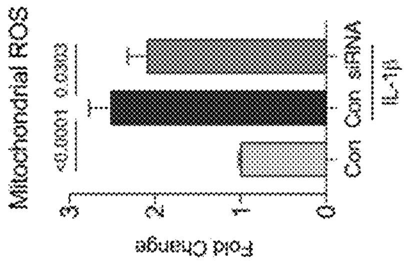
FIG. 6A-6E illustrate increase in MSCs cellular health upon USP16 downregulation.
Figure 6A:
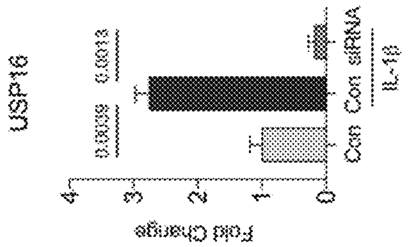
Figure 6C:
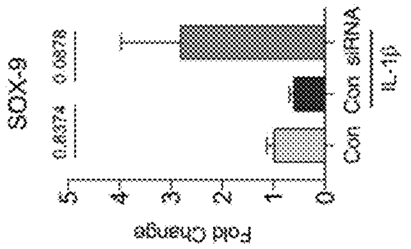
Figure 6D:
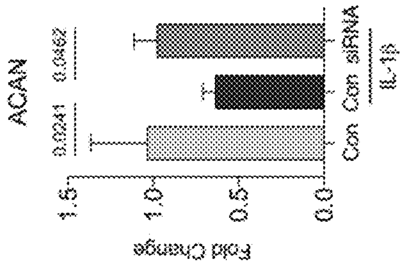
Figure 6E:
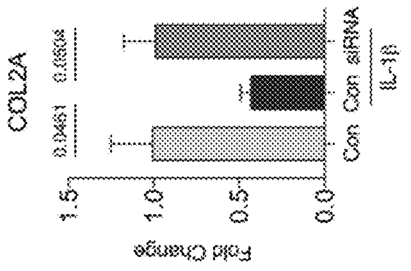
Figure 7:
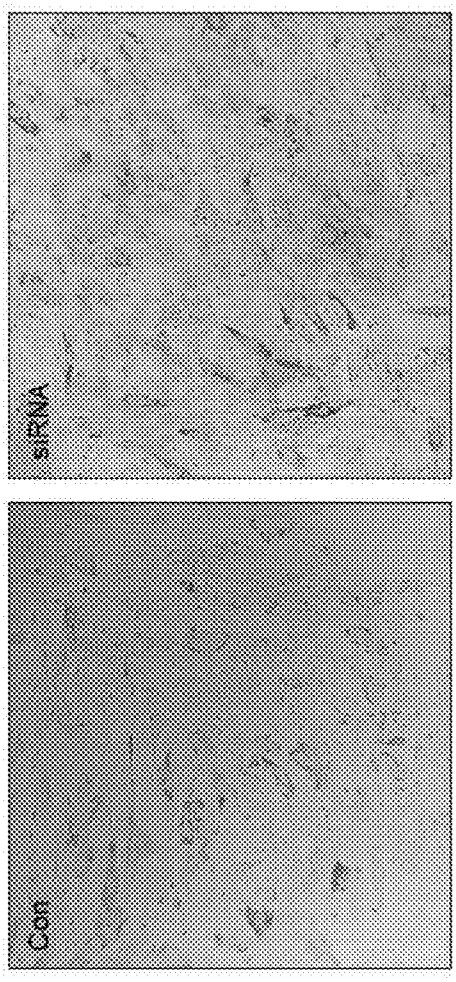
FIG. 7 illustrates MSCs cultured in chondrogenic differentiation medium for 21 days after USP16 knockdown and stained with Safranin-O as a surrogate for chondrogenic potential.

In an in vitro OA model, human MSCs were stimulated with IL-1β and at 24 hours a robust increase in USP16 gene expression was observed, suggesting that inflammatory stimuli present in the OA microenvironment may, albeit not directly, induce the expression of USP16 (FIG. 6A). Inflammation and reactive oxygen species are interdependent, each being the target of the other, and both may contribute to mesenchymal stem cells dysfunction. Moreover, the switch of energy supply from glycolysis to aerobic metabolism may be required for successful differentiation of MSCs, reinforcing the evidence that having healthy mitochondria is vital for MSC functions. Thus, mitochondrial health was assessed in the in vitro model described above, and IL-1β stimulation was observed to strongly increase MSCs mitochondrial ROS (FIG. 6B). When USP16 expression was downregulated in MSCs a reduction in mitochondrial ROS was observed. We also measured at the expression of SOX-9, the master regulator of chondrogenesis, and observed a strong activation upon USP16 downregulation, proving the critical role of USP16 in maintaining MSCs self-renewal (FIG. 6C). Knocking down USP16 in MSCs was observed to result in higher expression of collagen and proteoglycan genes, such as ACAN and COL2A (FIG. 6D, 6E). Finally, knocking down USP16 increased chondrogenic potential of MSCs and increased matrix deposition (FIG. 7). To assess the presence of glycosaminoglycans (GAGs), which are cartilage-specific matrix proteins MSCs that were differentiated for 21 days in chondrogenic medium were stained with Safranin-O. After removal of the culture medium, the cells were fixed in 4% paraformaldehyde for 30 min, then washed twice with PBS before the addition of 0.1% stock solutions of Safranin-G. After 30 min incubation at room temperature, the dye solution was removed, and the cells were washed with distilled water. Human articular chondrocytes were stained after 10 days in culture as above.

Figure 8:
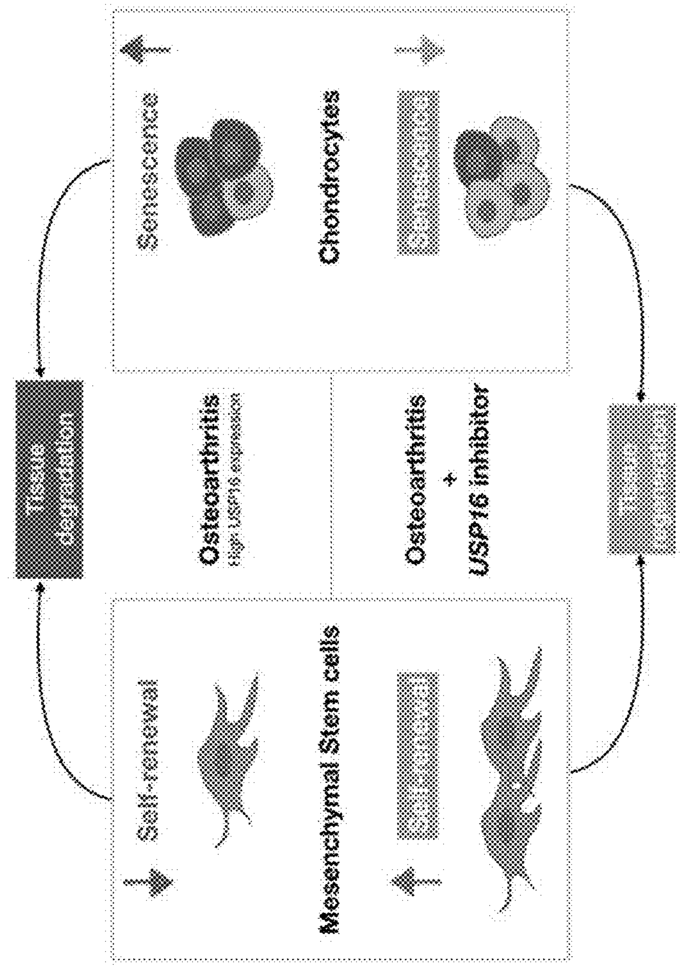
FIG. 8 illustrates the role of USP16 in tissue homeostasis in normal and OA joints. USP16 inhibition acts both on chondrocytes and MSCs to increase ECM.

USP16 is upregulated in human OA joints, in OA-derived chondrocytes and in BM-derived MSCs upon inflammatory stimuli. This upregulation has critical consequences on cellular health, in particular increased senescence, ROS production and decreased tissue homeostasis. Targeting USP16 protects both mesenchymal stem cells and chondrocytes thereby has therapeutic potential to modify OA disease progression by promoting regeneration and blocking senescence (FIG. 8).

Example 7: CRISPR Knockout of USP16 in HAC

HACs from both healthy and osteoarthritic (OA) affected individuals will be transfected once they reached at least 50% confluence. *Streptococcus pyogenes* Cas9-3NLS protein and all CRISPR and tracr RNAs as well as negative control CRISPR RNAs can be purchased from Synthego or Thermo Scientific Fischer. Table 1 provides guide sequences for knocking out USP16 which will be used with CRISPR.

TABLE 1

USP16 guide RNA sequences

| SEQ ID NO: | Description | Sequence |
|---|---|---|
| 1 | USP16 GUIDE 1 | GUGUGCAGACACAUUAGAAA |
| 2 | USP16 GUIDE 2 | UAUUGUCAGUCUUACAGUCU |
| 3 | USP16 GUIDE 3 | GUUUGGCUGUGUCUUAAAUG |

TABLE 1-continued

| USP16 guide RNA sequences | | |
|---|---|---|
| SEQ ID NO: | Description | Sequence |
| 4 | USP16 GUIDE T1 | UGGCGUCAGAUAGUGCUUCA |
| 5 | USP16 GUIDE T2 | GUGUUACGUAUGUGAUAAUG |

A cell viability/proliferation assay with CCK-8 reagent (Dojindo CK04-11) will be used to determine relative cell numbers of edited and non-edited cells. For this, 100 μl cell culture media of edited and non-edited cells (prior to the harvest of the endpoint analysis) is pipetted into 96 well plates in triplicates and 10 μl CCK-8 reagent is added and the plate was returned to the cell culture incubator. Media from edited and non-edited cells without the CCK-8 reagent, and media without cell layer but including CCK-8 reagent are used as negative controls. Two hours after addition of the reagent, the optical density (OD) is determined at 450 nm.

TABLE 2

| USP16 siRNA and shRNA sequences | | |
|---|---|---|
| SEQ ID NO | Description | Sequence |
| 6 | USP16 shRNA | TCCAGAAGGAATATCACTT |
| 7 | USP16 shRNA | 5'-GACTGTAAGACTGACAATAAA-3' |
| 8 | USP16 shRNA | 5'-TATATCAGTTCACCCGTAAT-3' |
| 9 | USP16 siRNA | 5'-GCCUAUGCCAAGGCAAGAA-3'; |
| 10 | USP16 siRNA | 5'-CCUCCUGUUCUUACUCUUCAUUUAA-3'; |
| 11 | USP16 siRNA | 5'-CCGGAAAUCUUAGAUUUGGCUCCUU-3' |
| 12 | USP16 siRNA | 5'-GGAUAAUGAUCUGGAGGUU-3' |
| 13 | USP16 siRNA | 5'-GAAUGAUAGUCAUACUCCU-3' |

Figure 9D:
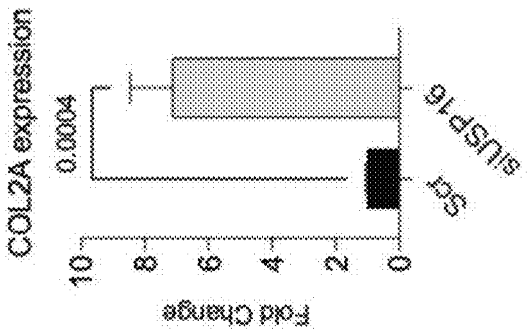
FIG. 9A-9D illustrate that USP16 knockdown in healthy mesenchymal stem cells (MSCs) improves markers of chondrogenesis by qRT-PCR measurements of SOX-9 (FIG. 9B), ACAN (FIG. 9C), and COL2A (FIG. 9D) gene expression in MSCs cultured in chondrogenic differentiation medium for 21 days after USP16 knockdown. Probability was determined by one-way ANOVA and Holm-Sidak's test for multiple comparisons between each treatment group. All data are shown as the mean±SEM and p values are indicated.
Figure 9C:
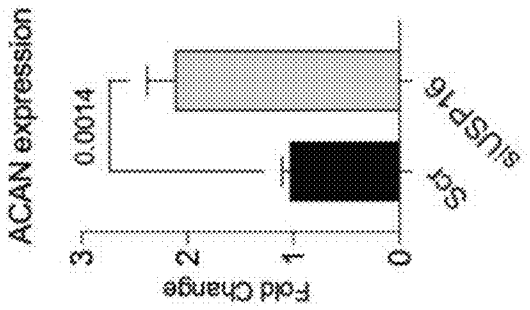
Figure 9B:
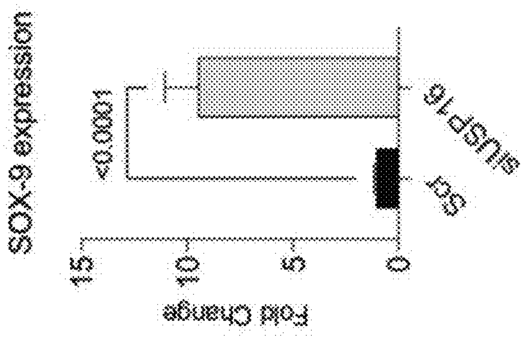
Figure 9A:
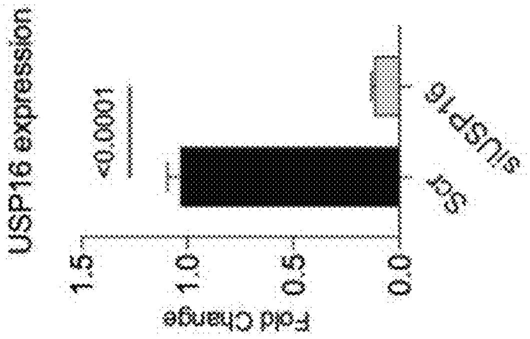

Example 8: USP16 Knockdown in Healthy MSCs Improves Markers of Chondrogenesis The qRT-PCR of USP16 expression (FIG. 9A), SOX-9 (FIG. 9B), ACAN (FIG. 9C), and COL2A (FIG. 9D) mRNA levels in MSCs were left in chondrogenic differentiation medium for 21 days. TARGETplus siRNA for USP16 (100 nM) was transfected in 2 healthy donor mesenchymal stromal cells in 2 technical repeats. T-test was used to calculate significance. All data are shown as the mean±s.d.

As illustrated in FIG. 9A-9D, USP16 knockdown in healthy MSCs improves markers of chondrogenesis.

Example 9: Downregulation of USP16 and Ubiquitination of Histone

Figure 10A:
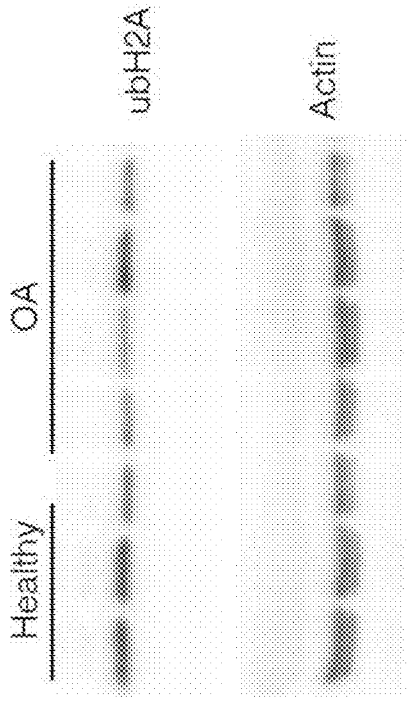
FIGS. 10A and 10B illustrate that H2AK119 ubiquitination is downregulated in OA chondrocytes compared to age-matched HD by WB analyses.
Figure 10B:
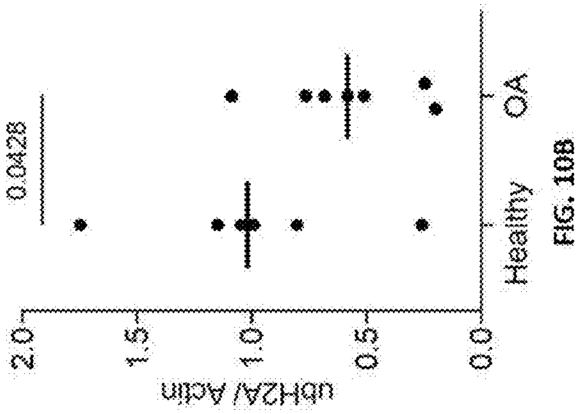

Human articular chondrocyte (HAC)s from both healthy and osteoarthritic (OA) affected individuals were cultured in chondrocyte growth medium as described above. After 10 days in culture, Western Blot analysis was performed to measure ubH2A levels (FIG. 10A). ON TARGETplus siRNA for USP16 (100 nM) was transfected in 3 healthy and 4 OA patient chondrocytes were analyzed in 3 technical replicates at passage 2 (FIG. 10B). Probability determined by one-way ANOVA and Holm-Sidak's test for multiple comparisons between each treatment group, as above. All data are shown as the mean±s.d., and p values are indicated.

As shown in FIGS. 10A and 10B, histone H2A ubiquitination is down-regulated in OA chondrocytes.

Figure 11:
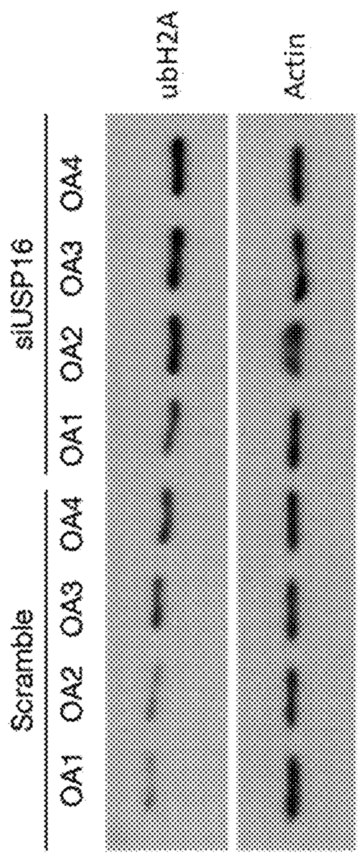
FIG. 11 illustrates that USP16 knockdown or downregulation by siRNA increases histone H2AK119 ubiquitination in OA chondrocytes.

Human articular chondrocyte (HAC)s from osteoarthritic (OA) affected individuals were cultured in chondrocyte growth medium as described above. After 10 days in culture, Western Blot analysis was performed to measure ubH2A levels (FIG. 11). ON TARGETplus siRNA for USP16 (100 nM) was transfected in 4 OA patient chondrocytes were analyzed at passage 2 (FIG. 11).

As shown in FIG. 11, histone H2A ubiquitination is increased in OA chondrocytes after reducing USP16 expression.

Example 10: USP16 Knockdown or Down-Regulation Improves OA Chondrocyte Proliferation Cellular proliferation was measured by counting the number of cells. ON TARGETplus siRNA for USP16 (100 nM) was transfected in 4 OA patient chondrocytes were analyzed in 3 technical replicates at passage 3. Probability determined by one-way ANOVA and Holm-Sidak's test for multiple comparisons between each treatment group, as above. All data are shown as the mean±s.d., and p values are indicated.

Figure 12:
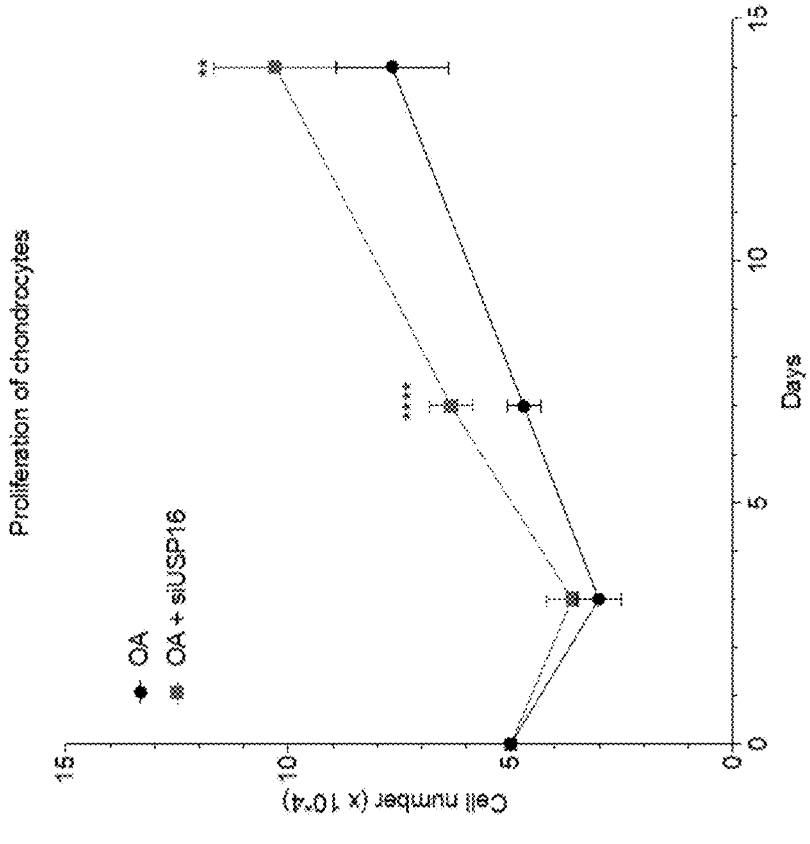
FIG. 12 illustrates that USP16 knockdown or downregulation improves the impaired ability of OA chondrocyte to proliferate. Probability was determined by t-test between each treatment group at each time point. All data are shown as the mean±SEM and p values are indicated (>0.005; **>0.0001).

As illustrated in FIG. 12, USP16 down-regulation increases proliferation of OA chondrocytes.

Example 11: USP16 Knockdown and Use of Compound 2 Targeting USP16 for the Reduction of Oxidative Stress in Healthy Chondrocytes LPS Stimulation Human articular chondrocytes (HAC) were transiently transfected with a siRNA control or targeting USP16 as described in Example 2. 36 hours post knockdown, cells were stimulated with LPS 1 μg/ml) for 48 h. Healthy Articular Chondrocytes (HACs) were pretreated with 0.1- and 1-μM Compound 2 for 1 h and then stimulated with LPS (1 μg/ml) for 48 h. At the end of the treatment, fluorescent dye, CM-H2DCFDA (final concentration 10 μl of 20 μM) was added to cells and incubated for 30 min in $CO_2$ incubator to measure the intracellular ROS produced in these cells. After incubation, the cells were washed with cold-phosphate buffered saline and the fluorescence intensity of the stained cells was measured at an excitation and emission wavelength of 485 nm and 530 nm respectively. Fluorescence intensity was then normalized for cell number using Hoechst staining.

LPS stimulation of chondrocytes was performed as described above.

Compound 2 has the chemical structure of

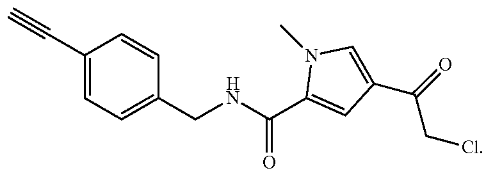 [SMILES: C#Cc1ccc(CNC(=O)c2cc(C(=O)CCl)cn2C)cc1]

Figure 13A:
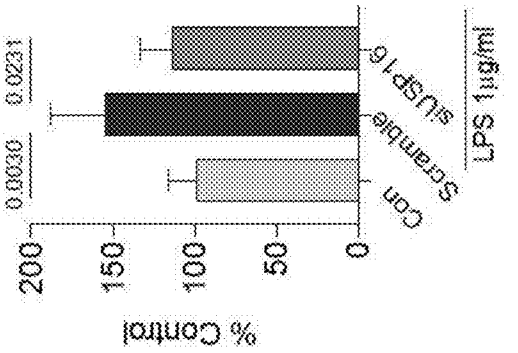
FIGS. 13A and 13B illustrate that siRNA-mediated silencing of USP16 (FIG. 13A) and small molecule targeting USP16 activity (Compound 2) (FIG. 13B) reduces inflammation-induced oxidative stress in healthy chondrocytes.

As illustrated in FIG. 13A, USP16 knockdown reduces inflammation induced oxidative stress in healthy chondrocytes.

Figure 13B:
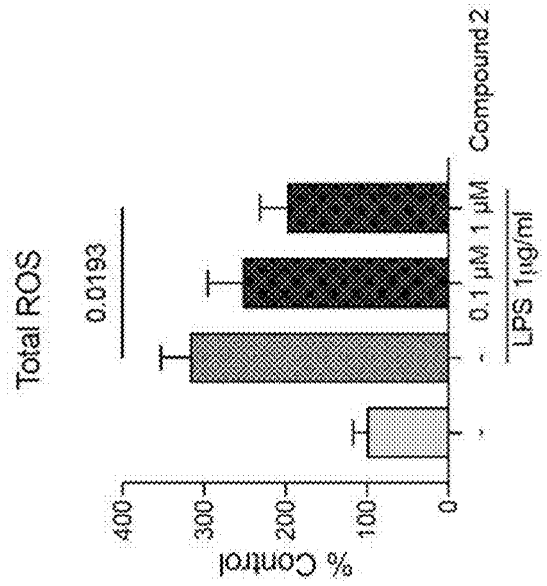

As illustrated in FIG. 13B, the use of Compound 2 at 0.1 μM and 1 μM concentrations targeting USP16 also reduced inflammation-induced oxidative stress in healthy chondrocytes in a dose-dependent manner.

Example 12: USP16 Knockdown Treatment Improves Pain Outcomes in Rat Medial Meniscal Tear-Induced-OA (MMT-OA) Model Animal Welfare All animals were handled humanely with due regard for their welfare. Every effort was made to minimize or eliminate pain and suffering of all the animals in the study. Animal care was following the recommendations of Committee for the Purpose of Control and Supervision of Experiments on Animals (CPCSEA), Government of India and Association for Assessment and Accreditation of Laboratory Animal Care International (AAALAC). The 'Form B' for carrying out animal experimentation was reviewed and approved by the Institutional Animal Ethics Committee (Syngene/IAEC/1088/09/2019).

Housing and Feeding

Animals were maintained in a controlled environment with 25° C. temperature, 20% humidity, a light/dark cycle of 12 hours each and 15-20 fresh air changes per hour. Animals were housed group wise (3 to 5 animals per cage) and autoclaved corncob was used as a bedding material. The animals were fed, ad libitum, with certified Irradiated Laboratory Rodent Diet (Altromin diet). Potable water, filtered through reverse osmosis, was autoclaved, and provided, ad libitum, to all animals via polycarbonate bottles fitted with stainless steel sipper tubes.

Animal Acclimatization and Grouping

All the animals were kept under acclimatization for a period of about 3 days before initiation of the experiment. One day prior to treatment, all the animals were randomized using Microsoft Excel based body weight stratification method. The weight variation of the animals did not exceed 20% of the mean body weight in a group at the time of randomization. Animals were assigned a temporary number at the base of tail using marker pen. Immediately after randomization, the animals were assigned a permanent number by ear notching. Cages were identified by cage cards indicating the study number, study code, group number, sex, dose, cage number, number of animals and animal number details.

Medical Meniscus Surgery

Medial meniscus surgery was performed on day 0, under isoflurane anaesthesia and aseptic conditions, the skin over the medial aspect of the right femoral-tibial joint was clipped to remove hair and surgically prepared using 70% alcohol and povidone-iodine. The medial collateral ligament was exposed by blunt dissection and transected to reflect the meniscus towards the femur. The joint space was visualized, and the meniscus was cut through the full thickness at its narrowest point to simulate a complete tear. The skin was closed using 4-0 silk suture. AAV2 injection, as described above, was performed on Day 3. Mechanical allodynia using Von Frey filaments was done by SUDO method (Aesthesio). Paw withdrawal threshold (PWT) was measured on, a day prior to MMT surgery (Basal values) and days 7, 14, 21, and 28 using manual von Frey filaments. PWT was measured using manual von Frey filaments (4, 10, 15, 26, 60 g; Aesthesio) following protocol reported in literature to assess changes in pain sensitivity.

AAV Injection

AAV2 virus was obtained from VectorBuilder, Inc., Chicago, IL. For intraarticular injections, 25 ul of virus containing $2.5*10^9$ vg was injected into the intraarticular space.

```
pAAV[shRNA]-EGFP-U6>rUsp16[shRNA#2]:
CTGAGTGTCCTAGAGATTTAA

pAAV[shRNA]-EGFP-U6>Scramble_shRNA:
CCTAAGGTTAAGTCGCCCTCG
```

Body Weight and Mortality

Bodyweight were recorded individually for all animals on the day of randomization, taken twice a week and on the day of termination. Animals were also observed for mortality at regular intervals. No signs of morbidity or distress were observed in any of the animals.

Mechanical Allodynia Using Von Frey Filaments

Mechanical allodynia using Von Frey filaments was done by SUDO method (Aesthesio). PWT was measured on, a day prior to MMT surgery (Basal values) and days 7, 14, 21 and 28 (one day prior to termination) using manual von Frey filaments. PWT was measured using manual von Frey filaments (4, 10, 15, 26, 60 g; Aesthesio) following protocol reported in literature (Bonin et al. 2014).

Termination and Tissue Collection

On day 28, animals were subjected to mild isoflurane anesthesia and blood was collected and plasma was stored at −80° C. for future analysis. The ipsilateral knee joint was collected for IHC and stored in 10% NBF for three animals each in sham and MMT control group, respectively. The markers MMP-13, CDKN2A, GFP and USP-16 were evaluated in IHC slides. From the remaining animals, cartilage (articular and medial meniscus) was collected for western blot analysis from the ipsilateral knee joint in sham and MNT operated knees and shipped to the client site. Synovial lavage from the ipsilateral and contralateral knee joints from the sham and MMT control groups were also collected.

Histopathology

Six weeks after surgery, the SD rats were sacrificed, and the affected knee joints were collected. The knee joints were fixed in 4% (v/v) paraformaldehyde for 1 day and then decalcified in 10% (v/v) EDTA for 2 weeks. After dehydration, the specimens were embedded in paraffin and cut into 3 m coronal sections. The tissue sections were stained with Toluidine blue (TB). The Osteoarthritis Research Society International scoring system was used to evaluate the medial tibial plateaus of the rats in each group.

Immunohistochemical Staining

After deparaffinization and rehydration, endogenous peroxidase activity in the sections was blocked with 3% hydrogen peroxide. Then, for antigen retrieval, the sections were incubated with 0.4% pepsin (Sigma-Aldrich) in 1 mM hydrochloric acid at 37° C. for 1 h. After blocking with 5% bovine serum albumin for 30 min at 37° C., the sections were incubated with primary antibody overnight at 4° C. and finally with an HRP-conjugated secondary antibody.

ELISA

Rat Cytokine Array/Chemokine Array 27 Plex (RD27) (Eve Technologies Corporation) was used to evaluate cytokine and growth factor expression in synovial fluid. Eotaxin, EGF, fractalkine, IFN-γ, IL-1α, IL-1β, IL-2, TL-4, TL-5, TL-6, IL-1β, IL-12(p70), IL-13, IL-17A, IL-18, IP-10, GRO/KC, TNF-α, G-CSF, GM-CSF, MCP-1, Leptin, LIX, MIP-1α, MIP-2, RANTES, and VEGF were targeted in this assay.

LPS Stimulation

Chondrocytes were pretreated with 0.1- and 1-μM CA for 1 h and then stimulated with LPS (1 μg/m)l for 48 h. For siRNA experiment, LPS stimulation was performed 36 hours after knockdown for additional 48 h. Fluorescent dye, CM-H2DCFDA (final concentration 10 μl of 20 μM) was added to cells and incubated for 30 min in $CO_2$ incubator to measure the intracellular ROS produced in these cells. After incubation, the cells were washed with cold-phosphate buffered saline and the fluorescence intensity of the stained cells was measured at an excitation and emission wavelength of 485 nm and 530 nm respectively. Fluorescence intensity was then normalized for cell number using Hoechst staining.

Statistical Analysis

Statistical analysis was performed using validated statistical software (GraphPad Prism 6). Data is represented as Mean±SEM. Number of animals in each group is represented as n. Two-way ANOVA followed by Dunnett's posttest was applied for body weight, mechanical allodynia ($p<0.05$; was considered significant). One-way ANOVA followed by Dunnett's multiple comparisons test was applied for histopathology scores, AUC pain scores ($p<0.05$; was considered significant). Student's t test was applied to compare individual treatment groups with the pathological control and $p<0.05$ was considered statistically significant.

Figure 14:
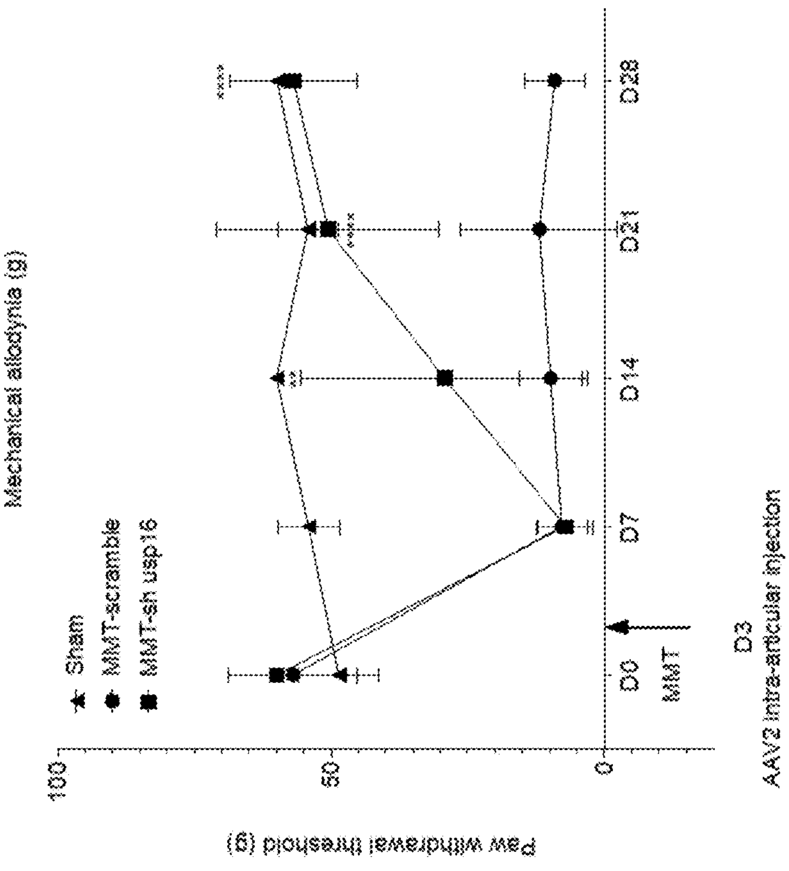
FIG. 14 illustrate that USP16 knockdown improves pain outcomes in rat Medial Meniscal Tear-Induced-OA (MMT-OA) model as measured by paw withdrawal threshold (mechanical allodynia). Probability was determined by t-test between each treatment group at each time point. All data are shown as the mean±SEM and p values are indicated (>0.005; **>0.0001).

As illustrated in FIG. 14, USP16 knockdown improves pain outcome as measured by paw withdrawal threshold in rat MMT-OA model after AAV2 intra-articular injection.

Figure 15B:
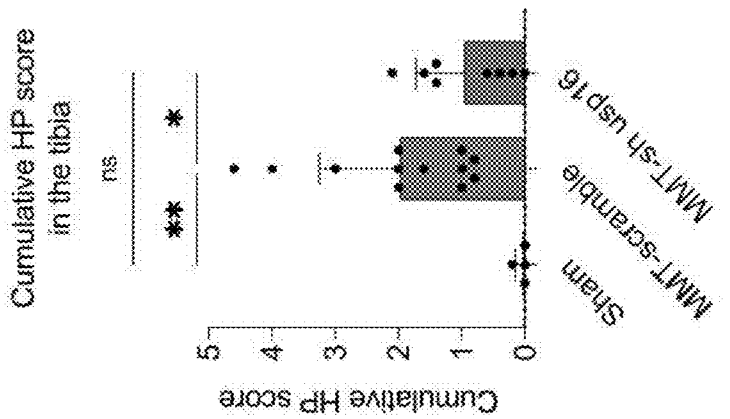
FIGS. 15A and 15B illustrate USP16 knockdown improves articular cartilage structural integrity in rat Medial Meniscal Tear-Induced-OA (MMT-OA) model.
Figure 15A:
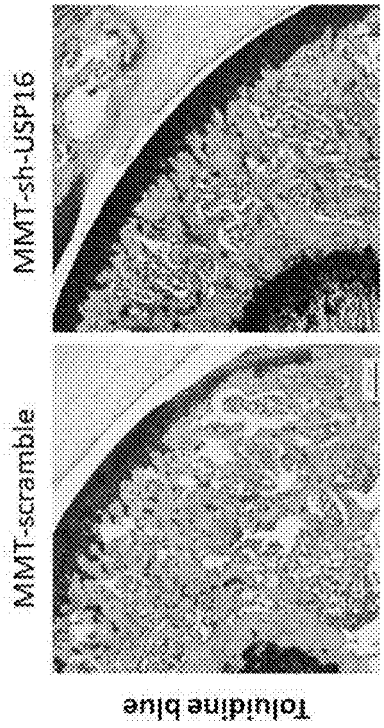

The degree and/or severity of MMT induced osteoarthritis was assessed semi-quantitatively using H&E and toluidine blue-stained joint sections for the articular cartilage alterations (score: 0-8), reduction/decrease in proteoglycan content (score: 0-6), chondrocyte cellularity (score: 0-3), tidemark integrity (score: 0-1) and synovial membrane integrity (score: 0-4). As illustrated in FIGS. 15A and 15B, USP16 knockdown improves cartilage structurally by increasing proteoglycan and synovial membrane integrity as well as decreasing cellularity at 28 days post MMT induction.

Figure 16B:
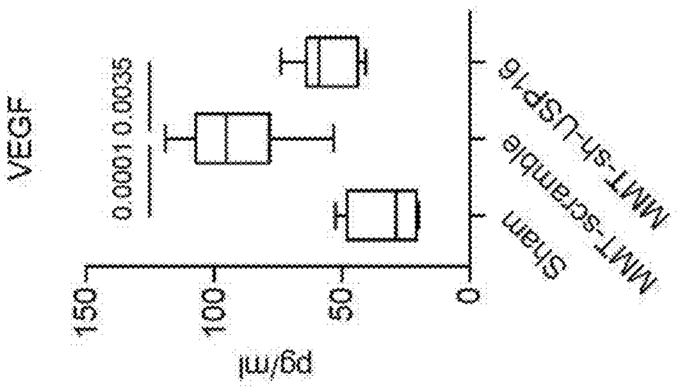
FIGS. 16A and 16B illustrate USP16 knockdown reduces the amount of inflammatory cytokines in synovial fluid of rat MMT-OA model measured by Rat Cytokine Array/Chemokine Array 27 Plex (RD27). Probability was determined by one-way ANOVA and Holm-Sidak's test for multiple comparisons between each treatment group. All data are shown as the mean±SEM and p values are indicated.
Figure 16A:
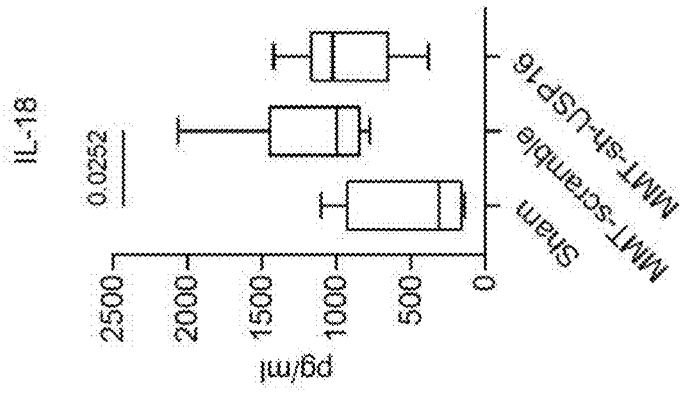

As illustrated in FIGS. 16A and 16B, synovial fluid was analyzed at termination for cytokines associated with OA progression at termination. USP16 knockdown reduces inflammatory markers of IL-18 (FIG. 16A) and VEGF (FIG. 16B) respectively in synovial fluid of rat MMT-OA model.

Figure 17A:
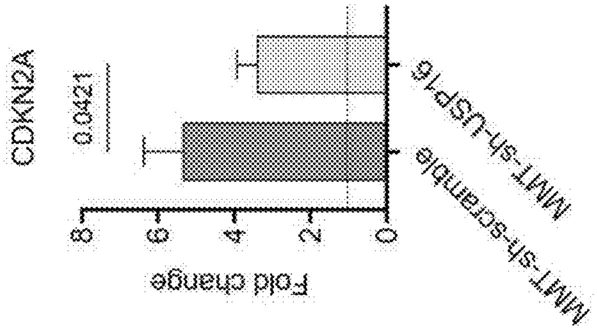
FIG. 17A-17C illustrate USP16 knockdown reduces CDKN2A (FIG. 17A) and MMP13 expression (FIG. 17B) and improves in ACAN expression (FIG. 17C) in rat MMT-OA model by measuring gene expression by qRT-PCR of the joint at the time of sacrifice. Probability was determined by one-way ANOVA and Holm-Sidak's test for multiple comparisons between each treatment group. All data are shown as the mean±SEM and p values are indicated.
Figure 17B:
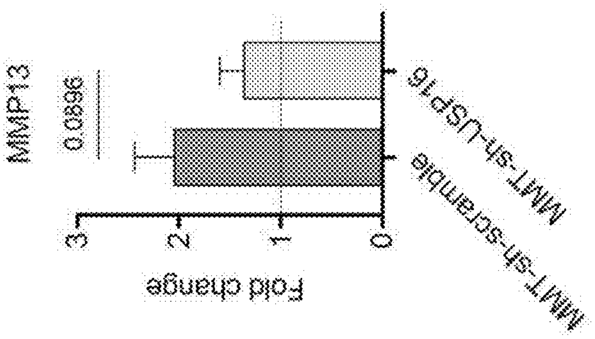
Figure 17C:
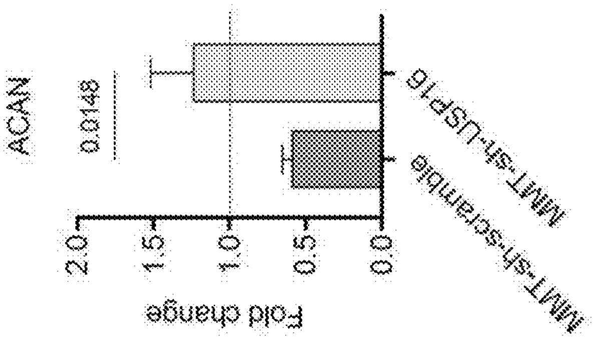

The qRT-PCR of CDKN2A expression (FIG. 17A), MMP-13 (FIG. 17B) and ACAN (FIG. 17C) mRNA levels in articular cartilage at 28 days post MMT induction was measured. Probability determined by one-way ANOVA and Holm-Sidak's test for multiple comparisons between each treatment group, as above. All data are shown as the mean±s.d., and p values are indicated. As illustrated in FIG. 17A-17C, USP16 knockdown reduces CDKN2A (FIG. 17A) and MMP13 (FIG. 17B) expressions and improves ACAN expression (FIG. 17C) in rat MMT-OA model.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating osteoarthritis in a subject in need thereof, the method comprising administering to the subject a therapeutically effective amount of a USP16 inhibitor.

2. The method of claim 1, wherein treating osteoarthritis comprises altering expression of an osteoarthritis marker.

3. The method of claim 2, wherein the osteoarthritis marker is selected from: a senescent marker selected from SA-β-gal, CDKN2D, CDKN2A, CDKN1B, and gamma-H2Ax; mitochondrial ROS; cellular ROS; mitochondrial membrane potential; a cartilage matrix degradation marker selected from MMP13, MMP1, MMP3, ADAM8, ADAM9, ADAM21, ADAMTS3, ADAMTS15, ADAMTS17, TIMP4, and SERPINA1; a cartilage matrix deposition marker selected from ACAN, COL2A, COL17A, COL28A1, COL10A, RUNX1, and RUNX2; an apoptosis marker selected from Caspase-6, Caspase-10, Caspase-12, BCL2, BCL6, BIRC3, and BAD; a cell cycle marker selected from CCND2, CCNA2, CCNB2, CCNB1, TOP2A, MKI67, BUB1, BUB1B, CDK6, RRM2, E2F2, and E2F1; a chondrogenic potential or a self-renewal marker selected from SOX-9, SOX-6, SOX-5, BIRC5, CENPU, BMP2, ALDH2, and ALDH4a1; and an inflammation marker selected from NF-KB, p105 and p65 phosphorylation, IKK, IL-IRA IL-1β, IL-6, IL-8, TNFa, IL-17, CCL5, CCR1, CCR2, CCR3, CCR5, MCP1, COX2, PGE2, CX3CL1, IL23a, and TNF.

4. The method of claim 2, wherein treating osteoarthritis comprises increasing the osteoarthritis marker, further wherein the osteoarthritis marker is selected from H2AK119 and H2AK118 ubiquitination.

5. The method of claim 2, wherein the osteoarthritis marker is assessed in cells biopsied from an affected joint of the subject, in extracellular matrix biopsied from an affected joint of the subject, or in synovial fluid, blood, or plasma collected from the subject.

6. The method of claim 1, wherein treating osteoarthritis comprises reversing or attenuating cartilage damage, increasing cartilage thickness in a joint, decreasing pain in an affected joint, increasing the joint space or reducing the joint space narrowing, decreasing swelling or inflammation in an affected joint, increasing mitochondrial membrane potential, decreasing mitochondrial ROS or cellular ROS, decreasing cartilage matrix degradation, improving an OARSI score of a joint, or improving a WOMAC score.

7. The method of claim 1, wherein the osteoarthritis is injury-induced osteoarthritis, age-induced osteoarthritis, diabetes-induced osteoarthritis, familial osteoarthritis, or idiopathic osteoarthritis.

8. The method of claim 1, wherein the USP16 inhibitor decreases markers of aging.

9. The method of claim 1, wherein the USP16 inhibitor increases markers of self-renewal.

10. The method of claim 1, wherein the subject is a mammal.

11. The method of claim 1, wherein the USP16 inhibitor is administered locally.

12. The method of claim 11, wherein the USP16 inhibitor is administered by an intra-articular injection.

13. The method of claim 1, wherein the USP16 inhibitor is administered orally.

14. A method of treating a disease or disorder in a subject in need thereof, the method comprising contacting a mesenchymal stem cell (MSC) with a USP16 inhibitor and administering the MSC to the subject.

15. A method of protecting chondrogenic potential or self-renewal in mesenchymal stem cells, the method comprising contacting the mesenchymal stem cells with an effective amount of a USP16 inhibitor.

16. A method of increasing cartilage production or proliferation of a chondrocyte or inhibiting senescence in a chondrocyte, the method comprising contacting the chondrocyte with an effective amount of a USP16 inhibitor.

17. The method of claim 1, wherein the USP16 inhibitor is a nucleic acid.

18. The method of claim 17, wherein the nucleic acid is an shRNA, an siRNA, a microRNA, or an asymmetric interfering RNA.

19. The method of claim 1, wherein the USP16 inhibitor is administered via a viral vector.

20. The method of claim 19, wherein the viral vector is selected from a retroviral vector, an adenoviral vector, and an adeno-associated viral vector.

* * * * *

SEQUENCE LISTING

```
Sequence total quantity: 15
SEQ ID NO: 1           moltype = RNA  length = 20
FEATURE                Location/Qualifiers
misc_feature           1..20
                       note = source = /note="Description of Artificial Sequence:
                        Synthetic oligonucleotide"
source                 1..20
                       mol_type = other RNA
                       organism = synthetic construct
SEQUENCE: 1
gtgtgcagac acattagaaa                                              20

SEQ ID NO: 2           moltype = RNA  length = 20
FEATURE                Location/Qualifiers
misc_feature           1..20
                       note = source = /note="Description of Artificial Sequence:
                        Synthetic oligonucleotide"
source                 1..20
                       mol_type = other RNA
                       organism = synthetic construct
SEQUENCE: 2
tattgtcagt cttacagtct                                              20

SEQ ID NO: 3           moltype = RNA  length = 20
FEATURE                Location/Qualifiers
misc_feature           1..20
                       note = source = /note="Description of Artificial Sequence:
                        Synthetic oligonucleotide"
source                 1..20
                       mol_type = other RNA
                       organism = synthetic construct
SEQUENCE: 3
gtttggctgt gtcttaaatg                                              20

SEQ ID NO: 4           moltype = RNA  length = 20
FEATURE                Location/Qualifiers
```

-continued

```
misc_feature          1..20
                      note = source = /note="Description of Artificial Sequence:
                       Synthetic oligonucleotide"
source                1..20
                      mol_type = other RNA
                      organism = synthetic construct
SEQUENCE: 4
tggcgtcaga tagtgcttca                                                 20

SEQ ID NO: 5          moltype = RNA  length = 20
FEATURE               Location/Qualifiers
misc_feature          1..20
                      note = source = /note="Description of Artificial Sequence:
                       Synthetic oligonucleotide"
source                1..20
                      mol_type = other RNA
                      organism = synthetic construct
SEQUENCE: 5
gtgttacgta tgtgataatg                                                 20

SEQ ID NO: 6          moltype = DNA  length = 19
FEATURE               Location/Qualifiers
misc_feature          1..19
                      note = source = /note="Description of Artificial Sequence:
                       Synthetic oligonucleotide"
source                1..19
                      mol_type = other DNA
                      organism = synthetic construct
SEQUENCE: 6
tccagaagga atatcactt                                                  19

SEQ ID NO: 7          moltype = DNA  length = 21
FEATURE               Location/Qualifiers
misc_feature          1..21
                      note = source = /note="Description of Artificial Sequence:
                       Synthetic oligonucleotide"
source                1..21
                      mol_type = other DNA
                      organism = synthetic construct
SEQUENCE: 7
gactgtaaga ctgacaataa a                                               21

SEQ ID NO: 8          moltype = DNA  length = 20
FEATURE               Location/Qualifiers
misc_feature          1..20
                      note = source = /note="Description of Artificial Sequence:
                       Synthetic oligonucleotide"
source                1..20
                      mol_type = other DNA
                      organism = synthetic construct
SEQUENCE: 8
tatatcagtt cacccgtaat                                                 20

SEQ ID NO: 9          moltype = RNA  length = 19
FEATURE               Location/Qualifiers
misc_feature          1..19
                      note = source = /note="Description of Artificial Sequence:
                       Synthetic oligonucleotide"
source                1..19
                      mol_type = other RNA
                      organism = synthetic construct
SEQUENCE: 9
gcctatgcca aggcaagaa                                                  19

SEQ ID NO: 10         moltype = RNA  length = 25
FEATURE               Location/Qualifiers
misc_feature          1..25
                      note = source = /note="Description of Artificial Sequence:
                       Synthetic oligonucleotide"
source                1..25
                      mol_type = other RNA
                      organism = synthetic construct
SEQUENCE: 10
cctcctgttc ttactcttca tttaa                                           25

SEQ ID NO: 11         moltype = RNA  length = 25
FEATURE               Location/Qualifiers
misc_feature          1..25
                      note = source = /note="Description of Artificial Sequence:
```

-continued

```
                       Synthetic oligonucleotide"
source                1..25
                      mol_type = other RNA
                      organism = synthetic construct
SEQUENCE: 11
ccggaaatct tagatttggc tcctt                                    25

SEQ ID NO: 12         moltype = RNA  length = 19
FEATURE               Location/Qualifiers
misc_feature          1..19
                      note = source = /note="Description of Artificial Sequence:
                       Synthetic oligonucleotide"
source                1..19
                      mol_type = other RNA
                      organism = synthetic construct
SEQUENCE: 12
ggataatgat ctggaggtt                                           19

SEQ ID NO: 13         moltype = RNA  length = 19
FEATURE               Location/Qualifiers
misc_feature          1..19
                      note = source = /note="Description of Artificial Sequence:
                       Synthetic oligonucleotide"
source                1..19
                      mol_type = other RNA
                      organism = synthetic construct
SEQUENCE: 13
gaatgatagt catactcct                                           19

SEQ ID NO: 14         moltype = DNA  length = 21
FEATURE               Location/Qualifiers
misc_feature          1..21
                      note = source = /note="Description of Artificial Sequence:
                       Synthetic oligonucleotide"
source                1..21
                      mol_type = other DNA
                      organism = synthetic construct
SEQUENCE: 14
ctgagtgtcc tagagattta a                                        21

SEQ ID NO: 15         moltype = DNA  length = 21
FEATURE               Location/Qualifiers
misc_feature          1..21
                      note = source = /note="Description of Artificial Sequence:
                       Synthetic oligonucleotide"
source                1..21
                      mol_type = other DNA
                      organism = synthetic construct
SEQUENCE: 15
cctaaggtta agtcgccctc g                                        21
```